United States Patent
Zadno-Azizi

(10) Patent No.: US 6,958,059 B2
(45) Date of Patent: Oct. 25, 2005

(54) METHODS AND APPARATUSES FOR DRUG DELIVERY TO AN INTRAVASCULAR OCCLUSION

(75) Inventor: Gholam-Reza Zadno-Azizi, Fremont, CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 195 days.

(21) Appl. No.: 10/035,389

(22) Filed: Dec. 28, 2001

(65) Prior Publication Data

US 2002/0062119 A1 May 23, 2002

Related U.S. Application Data

(63) Continuation-in-part of application No. 09/837,872, filed on Apr. 17, 2001, now abandoned, and a continuation-in-part of application No. 09/537,471, filed on Mar. 24, 2000, now Pat. No. 6,454,741, and a continuation-in-part of application No. 09/438,030, filed on Nov. 10, 1999, now Pat. No. 6,652,480, which is a continuation of application No. 09/415,607, filed on Oct. 8, 1999, now Pat. No. 6,217,567, and a continuation of application No. 09/314,054, filed on May 18, 1999, and a continuation-in-part of application No. 09/270,150, filed on Mar. 16, 1999, which is a continuation of application No. 09/049,857, filed on Mar. 27, 1998, now Pat. No. 6,135,991, and a continuation-in-part of application No. 09/049,712, filed on Mar. 27, 1998, now Pat. No. 6,544,276, which is a continuation-in-part of application No. 08/975,723, filed on Nov. 20, 1997, now Pat. No. 6,050,972, which is a continuation-in-part of application No. 08/813,807, filed on Mar. 6, 1997, now abandoned, which is a continuation-in-part of application No. 08/812,139, filed on Mar. 6, 1997, now abandoned, which is a continuation of application No. 08/812,876, filed on Mar. 6, 1997, now Pat. No. 6,068,623, which is a continuation of application No. 08/812,570, filed on Mar. 6, 1997, now Pat. No. 6,022,336, which is a continuation-in-part of application No. 08/650,464, filed on May 20, 1996, now abandoned.

(51) Int. Cl.$^7$ ............... A61M 31/00; A61M 37/00
(52) U.S. Cl. ................... 604/509; 604/103.01

(58) Field of Search ............ 604/96.01, 102.01, 604/103.01, 109, 164.13, 507, 508, 509, 915, 916, 917, 918, 919, 920, 921; 606/192, 193, 194, 195, 196, 197, 198, 199, 200; 600/434, 585

(56) References Cited

U.S. PATENT DOCUMENTS

| | | | |
|---|---|---|---|
| 2,356,659 | A | 8/1944 | De Paiva Aguiar |
| 3,173,418 | A | 3/1965 | Baran |
| 4,423,725 | A | 1/1984 | Baran et al. |
| 4,573,966 | A | 3/1986 | Weikl et al. |
| 4,610,662 | A | 9/1986 | Weikl et al. |
| 4,636,195 | A | 1/1987 | Wolinsky |

(Continued)

FOREIGN PATENT DOCUMENTS

| | | |
|---|---|---|
| EP | 0 402 467 | 12/1990 |
| EP | 0 526 102 | 2/1993 |
| EP | 0 526 102 A1 | 2/1993 |

(Continued)

OTHER PUBLICATIONS

U.S. Appl. No. 09/049,712, filed Mar. 27, 1998.
U.S. Appl. No. 09/438,030, filed Nov. 10, 1999.

Primary Examiner—Nicholas D. Lucchesi
Assistant Examiner—Mark K. Han
(74) Attorney, Agent, or Firm—Knobbe Martens Olson & Bear LLP

(57) ABSTRACT

A method for delivering a drug to the site of an intravascular occlusion. A guidewire having a balloon at one end is advanced across the occlusion using a guide catheter, and the balloon is inflated distal to the occlusion to occlude the blood vessel. An aspiration catheter is then inserted into the vessel with its tip less than about 5 mm from the surface of the balloon, and a drug is delivered which flows distal to proximal to treat the occlusion.

6 Claims, 14 Drawing Sheets

U.S. PATENT DOCUMENTS

| | | | |
|---|---|---|---|
| 4,696,668 A | | 9/1987 | Wilcox |
| 4,714,460 A | | 12/1987 | Calderon |
| 4,717,381 A | | 1/1988 | Papantonakos |
| 4,781,677 A | | 11/1988 | Wilcox |
| 4,824,436 A | | 4/1989 | Wolinsky |
| 4,867,742 A | | 9/1989 | Calderon |
| 4,909,258 A | | 3/1990 | Kuntz et al. |
| 4,911,163 A | | 3/1990 | Fina |
| 4,950,238 A | | 8/1990 | Sullivan |
| 4,968,306 A | | 11/1990 | Huss et al. |
| 5,049,132 A | | 9/1991 | Shaffer et al. |
| 5,059,178 A | | 10/1991 | Ya |
| 5,087,244 A | | 2/1992 | Wolinsky et al. |
| 5,092,841 A | * | 3/1992 | Spears .................. 604/103.01 |
| 5,135,484 A | | 8/1992 | Wright |
| 5,163,905 A | | 11/1992 | Don Michael |
| 5,163,906 A | | 11/1992 | Ahmadi |
| 5,184,627 A | | 2/1993 | de Toledo |
| 5,213,576 A | | 5/1993 | Abiuso et al. |
| 5,213,577 A | | 5/1993 | Kratzer |
| 5,256,141 A | | 10/1993 | Gencheff et al. |
| 5,279,546 A | | 1/1994 | Mische et al. |
| 5,295,962 A | | 3/1994 | Crocker et al. |
| 5,306,250 A | | 4/1994 | March et al. |
| 5,320,604 A | | 6/1994 | Walker et al. |
| 5,322,508 A | | 6/1994 | Viera |
| 5,342,306 A | | 8/1994 | Don Michael |
| 5,380,284 A | | 1/1995 | Don Michael |
| 5,395,311 A | | 3/1995 | Andrews |
| 5,397,307 A | | 3/1995 | Goodin |
| 5,411,466 A | | 5/1995 | Hess |
| 5,423,742 A | | 6/1995 | Theron |
| 5,439,446 A | | 8/1995 | Barry |
| 5,460,610 A | | 10/1995 | Don Michael |
| 5,462,529 A | * | 10/1995 | Simpson et al. ....... 604/101.04 |
| 5,478,309 A | | 12/1995 | Sweezer et al. |
| 5,505,700 A | | 4/1996 | Leone et al. |
| 5,505,701 A | | 4/1996 | Anaya Fernandez de Lomana |
| 5,514,092 A | | 5/1996 | Forman et al. |
| 5,554,114 A | | 9/1996 | Wallace et al. |
| 5,569,215 A | | 10/1996 | Crocker |
| 5,571,086 A | | 11/1996 | Kaplan et al. |
| 5,588,962 A | * | 12/1996 | Nicholas et al. ............ 604/507 |
| 5,599,307 A | | 2/1997 | Bacher et al. |
| 5,609,574 A | | 3/1997 | Kaplan et al. |
| 5,611,775 A | | 3/1997 | Machold et al. |
| 5,643,226 A | | 7/1997 | Cosgrove et al. |
| 5,653,689 A | | 8/1997 | Buelna et al. |
| 5,662,609 A | | 9/1997 | Slepian |
| 5,674,192 A | | 10/1997 | Sahatjian et al. |
| 5,674,198 A | | 10/1997 | Leone |
| 5,681,336 A | | 10/1997 | Clement et al. |
| 5,728,123 A | | 3/1998 | Lemelson et al. |
| 5,779,673 A | | 7/1998 | Roth et al. |
| 5,810,767 A | * | 9/1998 | Klein ......................... 604/509 |
| 5,833,644 A | | 11/1998 | Zadno-Azizi et al. |
| 5,833,650 A | | 11/1998 | Imran |
| 5,868,719 A | | 2/1999 | Tsukernik |
| 5,925,016 A | | 7/1999 | Chornenky et al. |
| 6,022,336 A | | 2/2000 | Zadno-Azizi et al. |
| 6,050,972 A | | 4/2000 | Zadno-Azizi et al. |
| 6,056,721 A | | 5/2000 | Shulze |
| 6,080,170 A | | 6/2000 | Nash et al. |
| 6,135,991 A | | 10/2000 | Muni et al. |
| 6,152,141 A | | 11/2000 | Stevens et al. |
| 6,217,567 B1 | | 4/2001 | Zadno-Azizi et al. |
| 6,295,989 B1 | | 10/2001 | Connors, III |
| 6,485,500 B1 | * | 11/2002 | Kokish et al. ............... 606/194 |

FOREIGN PATENT DOCUMENTS

| | | |
|---|---|---|
| EP | 0 770 405 A2 | 5/1996 |
| EP | 0 820 784 A2 | 8/1998 |
| WO | WO 83/01894 | 6/1983 |
| WO | WO 92/00113 | 1/1992 |
| WO | WO 95/01751 | 1/1995 |
| WO | WO 98/38929 | 9/1998 |
| WO | WO 98/38930 | 9/1998 |
| WO | WO 00/54673 | 9/2000 |
| WO | WO 01/70325 | 9/2001 |

* cited by examiner

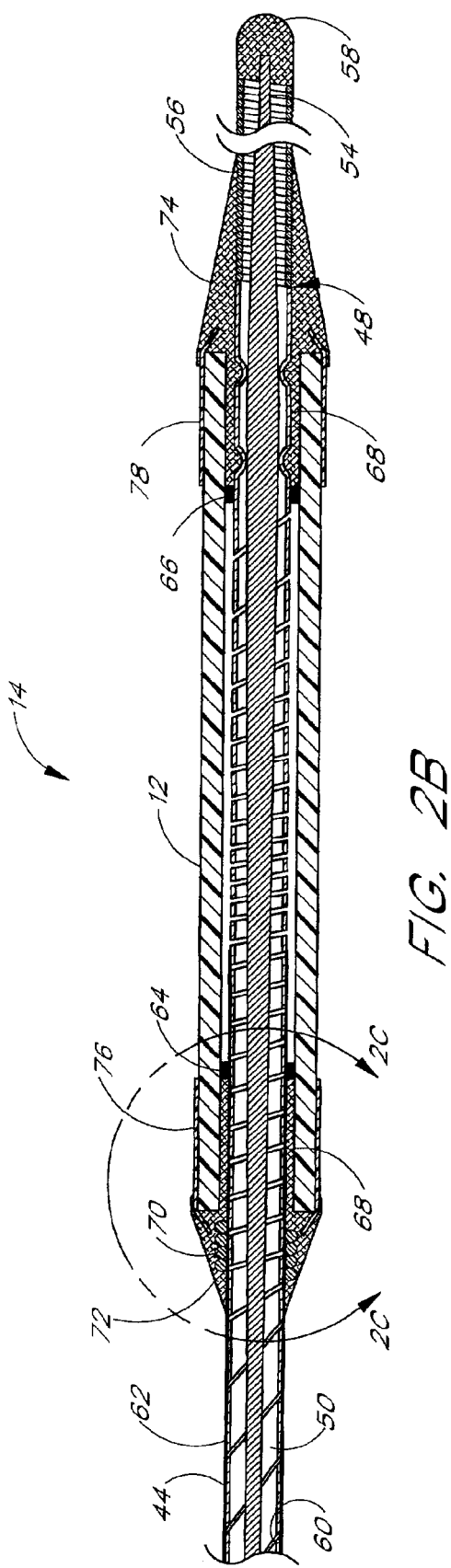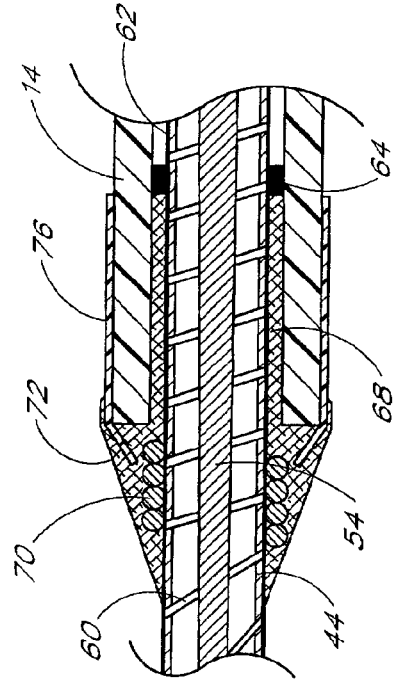

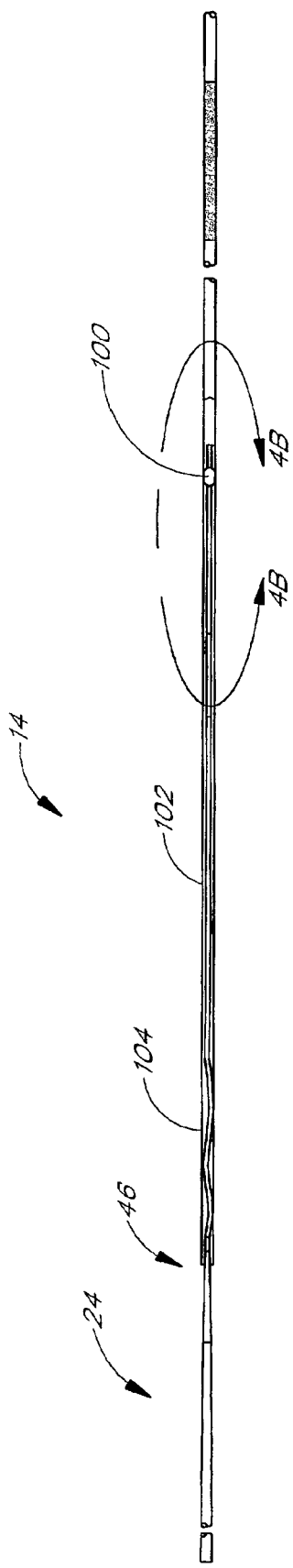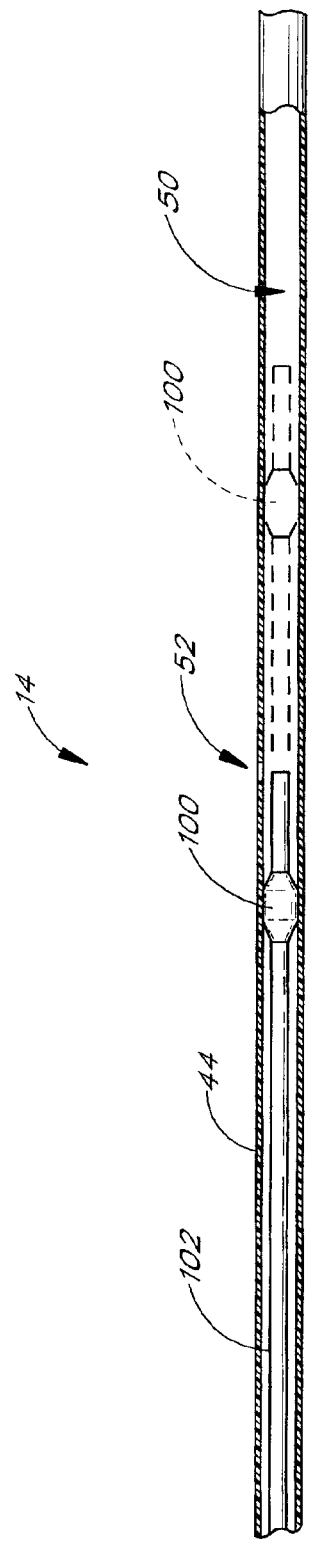
FIG. 4A
FIG. 4B

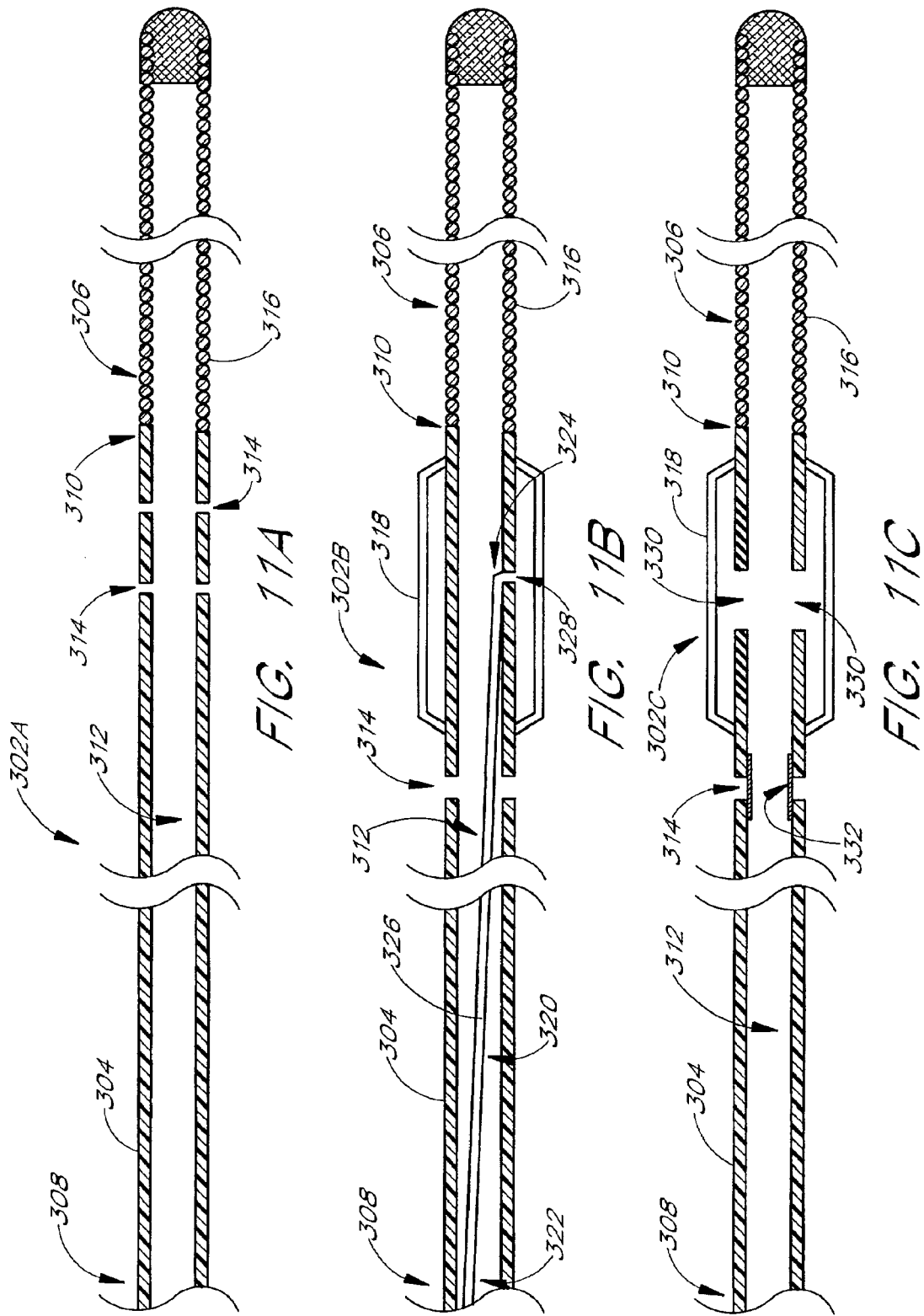

METHODS AND APPARATUSES FOR DRUG DELIVERY TO AN INTRAVASCULAR OCCLUSION

CROSS-REFERENCE TO RELATED APPLICATIONS

This application is a continuation-in-part of: U.S. application Ser. No. 09/537,471, filed Mar. 24, 2000, now U.S. Pat No. 6,454,741, which is a continuation of U.S. application Ser. No. 09/049,857, filed Mar. 27, 1998, now U.S. Pat. No. 6,135,991, which is a continuation-in-part of U.S. application Ser. No. 08/813,807, filed. Mar. 6, 1997, now abandoned; U.S. application Ser. No. 09/049,712, filed Mar. 27, 1998, now U.S. Pat No. 6,544,276, which is a continuation-in-part of U.S. application Ser. No. 08/975,723, filed Nov. 20, 1997, now U.S. Pat. No. 6,050,972, which is a continuation-in-part of U.S. application Ser. No. 08/812,139, filed Mar. 6, 1997, abandoned, which is a continuation-in-part of U.S. application Ser. No. 08/650,464 filed May 20, 1996, now abandoned; U.S. application Ser. No. 09/438,030, filed Nov. 10, 1999, now U.S. Pat No. 6,652,480; U.S. application Ser. No. 09/270,150, filed Mar. 16, 1999, now abandoned; U.S. application Ser. No. 09/837,872, filed Apr. 17, 2001, now abandoned, which is a continuation of U.S. application Ser. No. 09/415,607, filed Oct. 8, 1999, now U.S. Pat. No. 6,217,567, which is a continuation of U.S. application Ser. No. 08/812,876, filed Mar. 6, 1997, now U.S. Pat. No. 6,068,623; and U.S. application Ser. No. 09/314,054, filed May 18, 1999, now abandoned, which is a continuation of U.S. application Ser. No. 08/812,570, filed Mar. 6, 1997, now U.S. Pat. No. 6,022,336, which is a continuation-in-part of U.S. application Ser. No. 08/650,464, filed May 20, 1996, now abandoned; all of which are incorporated by reference in their entireties.

BACKGROUND OF THE INVENTION

1. Field of the Invention

Certain embodiments disclosed relate to delivery of drugs to the site of an intravascular occlusion using an aspiration or other catheter. The method is particularly well suited for treating stenoses or occlusions within saphenous vein grafts, coronary arteries, cerebral arteries and similar vessels.

2. Description of the Related Art

Human blood vessels often become occluded or completely blocked by plaque, thrombi, emboli or other substances, which reduces the blood carrying capacity of the vessel. Should the blockage occur at a critical location in the circulation, serious and permanent injury, or death, can occur. To prevent this, some form of medical intervention is usually performed when significant occlusion is detected, such as during an acute myocardial infarction (AMI).

Coronary heart disease is the leading cause of death in the United States and a common occurrence worldwide. Damage to or malfunction of the heart is caused by narrowing or blockage of the coronary arteries (atherosclerosis) that supply blood to the heart. The coronary arteries are first narrowed and may eventually be completely blocked by plaque, and may further be complicated by the formation of thrombi (blood clots) on the roughened surfaces of the plaques. AMI can result from atherosclerosis, especially from an occlusive or near occlusive thrombus overlying or adjacent to the atherosclerotic plaque, leading to death of portions of the heart muscle. Thrombi and emboli also often result from myocardial infarction, and these clots can block the coronary arteries, or can migrate further downstream, causing additional complications.

The carotid arteries are the main vessels which supply blood to the brain and face. The common carotid artery leads upwards from the aortic arch, branching into the internal carotid artery which feeds the brain, and the external carotid artery which feeds the head and face. The carotid arteries are first narrowed and may eventually be almost completely blocked by plaque, and may further be complicated by the formation of thrombi (blood clots) on the roughened surfaces of the plaques. Narrowing or blockage of the carotid arteries is often untreatable and can result in devastating physical and cognitive debilitation, and even death.

Various types of intervention techniques have been developed which facilitate the reduction or removal of the blockage in the blood vessel, allowing increased blood flow through the vessel. One technique for treating stenosis or occlusion of a blood vessel is balloon angioplasty. A balloon catheter is inserted into the narrowed or blocked area, and the balloon is inflated to expand the constricted area. In many cases, near normal blood flow is restored. It can be difficult, however, to treat plaque deposits and thrombi in the coronary arteries, because the coronary arteries are small, which makes accessing them with commonly used catheters difficult. Other types of intervention include atherectomy, deployment of stents, introduction of specific medication by infusion, and bypass surgery.

Furthermore, the fear of dislodging an embolus from an ulcerative plaque and the severe resulting consequences has prevented the widespread use of angioplasty in the carotid arteries. Because of the potential complications, the options for minimally invasive treatment of the carotid arteries are severely limited.

Carotid endarterectomy is another type of intervention for removal of blockages from the carotid arteries. In endarterectomy, the carotid bifurcation is exposed through an incision in the neck of the patient. Clamps are placed on either side of the occlusion to isolate it, and an incision made to open the artery. The occlusion is removed, the isolated area irrigated and aspirated, and the artery sutured closed. The clamps are removed to reestablish blood flow through the artery. In carotid endarterectomy, the emboli and debris are contained and directed by activating and deactivating the clamps. For example, after the clamps are in place, one on the common carotid artery and one on the internal carotid artery, the particles are contained between the two clamps. After the occlusion is removed, the clamp on the common carotid artery is opened, allowing blood to flow into the previously isolated area toward the clamp on the internal carotid. This blood flow is then aspirated through an external aspiration tube. The common carotid artery is then reclamped, and the clamp on the internal carotid opened. This causes blood to flow into the previously isolated area toward the clamp on the common carotid artery. The flow is then aspirated. The clamp on the internal carotid artery is closed, and the artery is sutured closed. This method allows for the flushing of debris into the area where aspiration occurs.

Alternatively, this method of clamping and unclamping the carotid arteries can be done after the incision in the artery is sutured closed. Using this method, it is hoped that any particles in the internal carotid artery will be forced back to the common carotid artery, then into the external carotid area, where serious complications are unlikely to arise from emboli.

Carotid endarterectomy is not without the serious risk of embolization and stroke caused by particles of the blocking material and other debris moving downstream to the brain, however.

There is therefore a need for improved methods of treatment of occluded vessels which decrease the risks to the patient.

SUMMARY OF THE INVENTION

In one embodiment of the present invention, a method is provided for treating an intravascular occlusion. The method comprises delivering fluid containing an occlusion-treating drug at a location proximal to an intravascular occlusive device. The occlusive device may be a balloon, while the drug may be a thrombolytic agent, an anticoagulant or a radioisotope. The occlusive device is preferably delivered on a guidewire, with the occlusive device being actuated once the device is delivered distal to the occlusion. The drug is preferably delivered at a rate of between about 0.1 and 10 cc/second. In one embodiment, the drug travels proximally to distally, and once the drug or at least a portion thereof contacts the device, the drug or portion thereof travels in a distal to proximal direction, i.e., against the flow of blood. Correspondingly, because blood is flowing proximally to distally in the vessel, the blood flow localizes the drug at a desired treatment site in order to treat the occlusion.

The fluid-containing drug is preferably delivered through a catheter riding over the guidewire. In one embodiment, the catheter is an aspiration catheter. This allows the same lumen used for delivering drugs to aspirate any particles broken off by the drug treatment. Because the occlusive device is preferably actuated continuously during both drug delivery and aspiration, by delivering drugs and aspirating through the same catheter, the time that the occlusive device remains inflated is minimized.

In another embodiment of the present invention, a method for treating an intravascular occlusion comprises delivering an occlusive device at its distal end into a blood vessel to a site near said occlusion. A catheter having a proximal end and distal end is delivered to the site of said occlusion such that the distal end of the catheter is proximal to the occlusive device. The occlusive device on the guidewire is actuated at a location distal to said occlusion to at least partially occlude blood flow through the vessel. A drug-containing fluid is delivered from the distal end of the catheter such that at least a portion of the drug-containing fluid contacts the occlusive device.

In another embodiment of the present invention, a method of treating an intravascular occlusion in a blood vessel comprises delivering a guidewire having an occlusive device to the site of the occlusion such that the occlusive device is distal to the occlusion. A catheter is delivered having a proximal end and a distal end and a lumen extending therethrough to the site of the occlusion such that the distal end of the catheter is proximal to the occlusive device. The occlusive device is actuated to at least partially obstruct blood flow through the blood vessel. A treatment fluid is delivered through the lumen of the catheter such that the fluid flows in a proximal to distal direction out of the distal end of the catheter, and then flows in a distal to proximal direction after contacting the occlusive device. Particles generated by the action of the treatment fluid on the occlusion are aspirated through the lumen of the catheter at the distal end.

In another embodiment of the present invention, a method for crossing an intravascular occlusion in a blood vessel is provided. The method comprises delivering a hollow wire in a proximal to distal direction past the occlusion, and delivering fluids through a lumen in said hollow wire to dissolve the occlusion while crossing of the occlusion with the hollow wire.

In another embodiment of the present invention, a method for treating an intravascular occlusion, comprises delivering a catheter having a proximal end and a distal end and a lumen extending therethrough into a blood vessel to a site near said occlusion. The catheter has an occlusive device on the distal end. The occlusive device is actuated at a location distal to the occlusion to at least partially occlude blood flow through said vessel. A drug-containing fluid is injected through the lumen of the catheter across said occlusion in a distal to proximal direction. In one embodiment, the drug-containing fluid is delivered through a plurality of holes in the catheter proximal to the occlusive device. In another embodiment, the drug-containing fluid is delivered through a plurality of holes in a proximal face of an occlusive balloon.

BRIEF DESCRIPTION OF THE DRAWINGS

FIG. 2B is a longitudinal cross-sectional view of the distal end of the balloon catheter of FIG. 2A.

FIG. 2C is an enlarged cross-sectional view of the proximal end of the balloon of FIG. 2B.

FIG. 4A is a partial cross-sectional view of a low profile catheter valve.

FIG. 4B is an enlarged view of the low profile catheter valve of FIG. 4A, showing the valve in an open position (and a closed position shown in phantom).

FIGS. 11A–11C are schematic cross-sectional views of alternative embodiments of a hollow catheter having holes, valves, and the like, to permit the escape of irrigation or other fluids.

DETAILED DESCRIPTION OF THE PREFERRED EMBODIMENTS

Certain preferred embodiments of the present invention provide methods for localized drug delivery in high concentration to the site of an intravascular occlusion by using an aspiration catheter for both aspiration and drug delivery. This method is used either alone, or in combination with a therapy catheter as discussed below. The drug delivery method may be used in conjunction with any method for preventing distal embolization during removal of plaque, thrombi or other occlusions from a blood vessel. A preferred embodiment of the present invention is adapted for use in the treatment of a stenosis or an occlusion in a blood vessel in which the stenosis or occlusion has a length and a width or thickness which at least partially occludes the vessel's lumen. Thus, the method is effective in treating both partial and complete occlusions of blood vessels.

It is to be understood that "occlusion" as used herein with reference to a blood vessel is a broad term and is used in its ordinary sense and includes both complete and partial occlusions, stenoses, emboli, thrombi, plaque and any other substance which at least partially occludes the lumen of the blood vessel. The term "occlusive device" as used herein is a broad term and is used in its ordinary sense and includes balloons, filters and other devices which are used to partially or completely occlude the blood vessel prior to performing therapy on the occlusion. It will be appreciated that even when a filter is used, the filter may be partially or completely occlusive.

The term "drugs" as used herein is a broad term and is used in its ordinary sense and includes genes and cells. The methods of the present invention are particularly suited for use in removal of occlusions from saphenous vein grafts, coronary and carotid arteries, and vessels having similar pressures and flow.

I. Overview of Occlusion System

A. Balloon System

Figure 1:
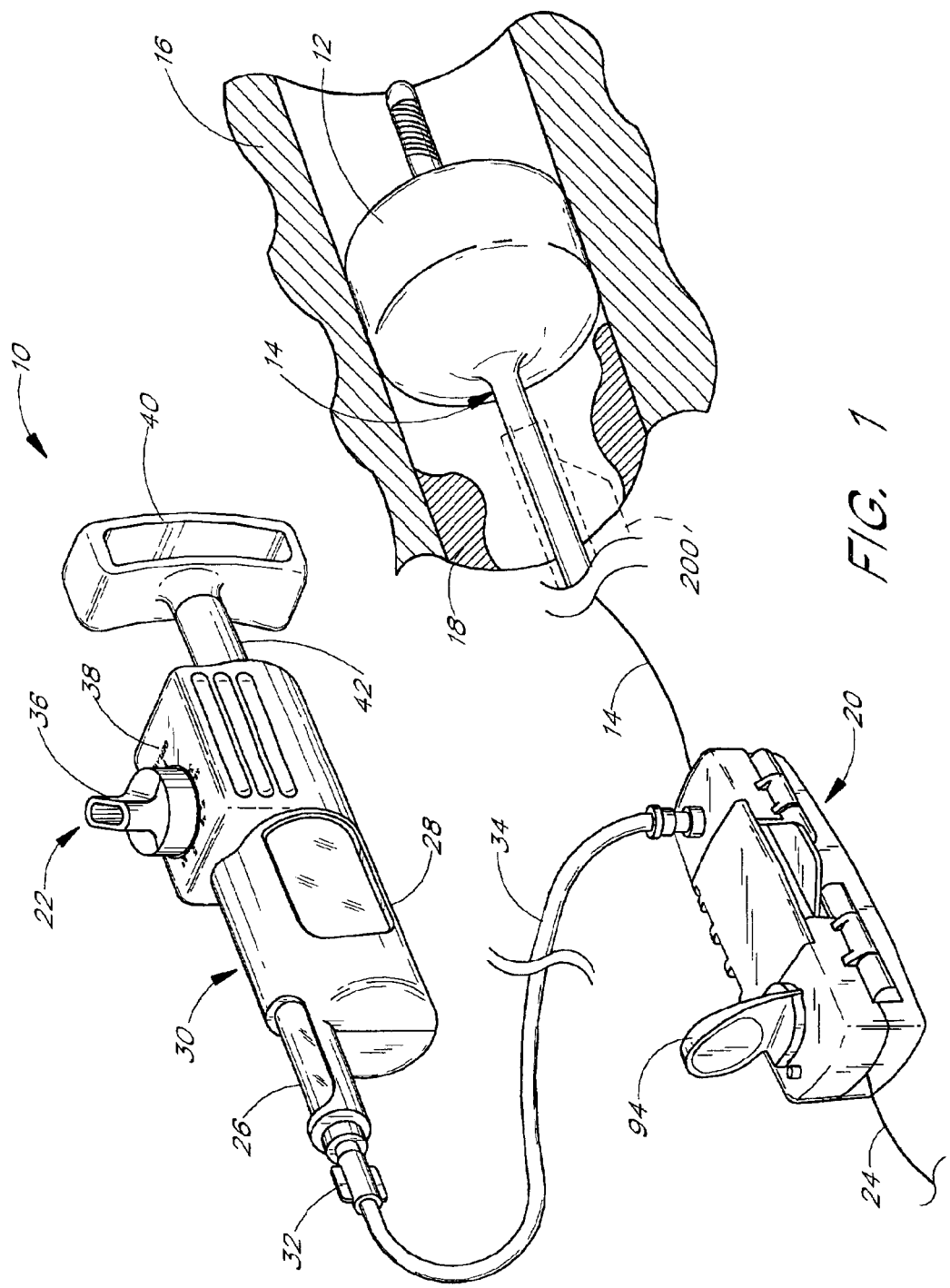
FIG. 1 is a perspective view of an integrated inflation/deflation device, shown operably coupled to an illustrative inflation adapter and a balloon catheter deployed in a blood vessel.

FIG. 1 illustrates generally the components of one exemplifying occlusion balloon guidewire system 10. As described in further detail below, an occlusion balloon 12 used in this system is delivered on a guidewire 14 to a location in a blood vessel 16 distal an occlusion 18. Through the use of an adapter 20 and an inflation/deflation device or syringe assembly 22, the balloon is inflated through a lumen in the guidewire 14 to occlude the vessel distal to the occlusion. Through the use of a valve 24 described below, the adapter 20 can be removed from the proximal end of the guidewire 14 while the balloon 12 remains inflated. With the proximal end of the guidewire free of obstructions, various therapy and other catheters can be delivered and exchanged over the guidewire 14 to perform treatment on the occlusion 18. Because the balloon 12 on the guidewire 14 remains inflated distal to the occlusion 18, any particles broken off by treating the occlusion 18 are isolated proximal to the balloon. These particles can be removed using an aspiration catheter 200 (shown in phantom in FIG. 1) delivered over the guidewire. After the particles are removed, the adapter 20 and inflation/deflation device 22 can be reattached to the proximal end of the guidewire to deflate the balloon.

B. Syringe Assembly

Preferred embodiments of the present invention may comprise or be used in conjunction with a syringe assembly as described in U.S. Pat. No. 6,234,996, the entirety of which is incorporated herein by reference in its entirety. One preferred syringe assembly is available from Medtronic PercuSurge, Inc. of Sunnyvale, Calif. under the name EZ FLATOR™.

One preferred embodiment of a syringe assembly 22 for inflation and deflation of an occlusion balloon is shown in FIG. 1. The syringe assembly 22 comprises a low-volume inflation syringe 26 and a high capacity or reservoir syringe 28 encased together in a housing 30. The syringe assembly 22 is preferably attached via a connector 32 and a short tube 34 to an adapter 20 within which a low profile catheter valve 24 and a balloon catheter 14 are engaged during use. The balloon catheter is shown in an inflated state within a blood vessel in FIG. 1 An inflation/deflation knob 36 is disposed on the outside of the housing 30. Indicia 38 are preferably located on the housing 30 adjacent the knob 36 so that a clinician using the device can monitor the precise volume of liquid delivered by the inflation syringe 22. As depicted, the indicia 38 preferably comprise numbers corresponding to the size and shape of the balloon used. When the knob 38 is rotated from the "DEFLATE" or "0:" position to the number corresponding to the balloon in use, the syringe assembly 22 delivers the fluid volume associated with that balloon size. Alternatively, the indicia 38 could indicate the standard or metric volume of fluid delivered at each position. A handle 40 is formed at a proximal end of the plunger 42. Preferably, the handle 40 is large, as illustrated in FIG. 1, and is easily held in a clinician's hand.

C. Occlusion Balloon Guidewire

The occlusion balloon guidewire system generally illustrated in FIG. 1 performs the function of occluding a vessel and allowing for the slidable insertion or advancement of various other catheters and devices. The term "catheter" as used herein is therefore intended to include both guidewires and catheters with these desired characteristics.

Figure 2A:
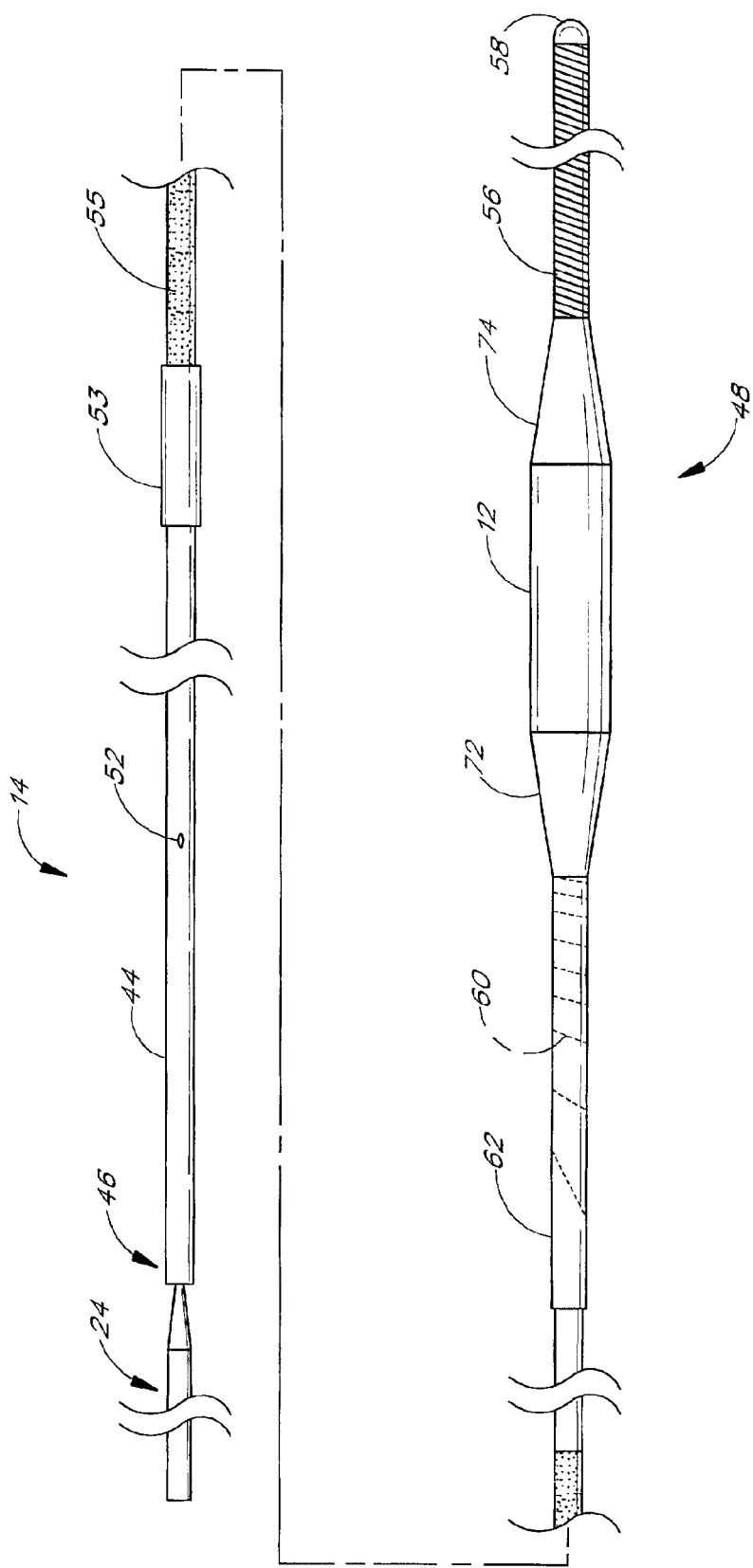
FIG. 2A is a side view of a balloon catheter which can be used in accordance with one preferred embodiment of the present invention.

As shown in FIG. 2A, a balloon guidewire catheter 14 generally comprises an elongate flexible tubular body 44 extending between a proximal control end 46, corresponding to a proximal section of the tubular body 44, and a distal functional end 50 (not shown), corresponding to a distal section of tubular body 44. Tubular body 44 has a central lumen 48, which extends between the proximal and distal ends. An inflation port 52, shown also in FIGS. 4A and 4B described below, is provided on tubular body 44 near the proximal end 46. Inflation port 52 is in fluid communication with lumen 50 such that fluid passing through inflation port 52 into or out of the lumen 50 may be used to inflate or deflate an inflatable balloon 12 in communication with lumen 50.

A valve 24, as described below, is inserted into the proximal end 46 of the tubular body 44 to control inflation of a balloon 12 mounted on the distal end of the tubular body through inflation notch 52. The inflation notch 52 is preferably formed by electric discharge machining (EDM). A proximal marker 53, which is preferably made of gold, is placed over the tubular body 44 distal to the inflation notch 52. Distal to the marker 53, a nonuniform coating 55 of polymer material, more preferably polytetrafluoroethylene (TFE), is applied to the tubular body 44, terminating proximal to a shrink tubing 62. The shrink tubing 62 extends up to and within the balloon 12, as described below. Adhesive tapers 72 and 74 extend from the proximal and distal ends of the balloon, respectively. The proximal taper 72 preferably extends from the proximal end of the balloon to the shrink tubing 62 on the tubular body 44, while the distal taper 74 extends to coils 56 extending from the distal end 48 of the tubular body 44. The coils 52 terminate in a distal ball 58.

The length of the tubular body 44 may be varied considerably depending on the desired application. For example, when catheter 14 serves as a guidewire for other catheters in a conventional percutaneous transluminal coronary angioplasty procedure involving femoral artery access, tubular body 44 is comprised of a hollow hypotube having a length in the range from about 160 to about 320 centimeters, with a length of about 180 centimeters being optimal for a single operator device, or 300 centimeters for over the wire applications. Alternatively, for a different treatment procedure not requiring as long a length of tubular body 44, shorter lengths of tubular body 44 may be provided.

Tubular body 44 generally has a circular cross-sectional configuration with an outer diameter within the range from about 0.008 inches to 0.14 inches. In applications where catheter 14 is to be used as a guidewire for other catheters, the outer diameter of tubular body 44 ranges from 0.010 inches to 0.038 inches and preferably is about 0.014 to 0.020 inches in outer diameter or smaller. Noncircular cross-sectional configurations of lumen 50 can also be adapted for use with the catheter 14. For example, triangular, rectangular, oval and other noncircular cross-sectional configurations are also easily incorporated for use with the preferred embodiments, as will be appreciated by those of skill in the art. The tubular body 44 may also have variable cross-sections.

The tubular body 44 has sufficient structural integrity or "pushability" to permit catheter 14 to be advanced through the vasculature of a patient to distal arterial locations without buckling or undesirable kinking of tubular body 44. It is also desirable for the tubular body 44 to have the ability to transmit torque such as in those embodiments where it may be desirable to rotate tubular body after insertion into a patient. A variety of biocompatible materials known by those of skill in the art to possess these properties and to be suitable for catheter manufacture may be used to produce tubular body 44. For example, tubular body 44 may be made of a stainless steel material such as ELGILOY™. or may be made of polymeric material such as PEEK, nylon, polyimide, polyamide, polyethylene or combinations thereof In one preferred embodiment, the desired properties of structural integrity and torque transmission are achieved by forming the tubular body 44 out of an alloy of titanium and nickel, commonly referred to as nitinol. In a more preferred embodiment, the nitinol alloy used to form the tubular body 80 is comprised of about 50.8% nickel and the balance titanium, which is sold under the trade mark TINEL™ by Memry Corporation. It has been found that a catheter tubular body having this composition of nickel and titanium exhibits an improved combination of flexibility and kink-resistance in comparison to other materials.

Other details regarding construction of balloon guidewire catheters may be found in assignee's U.S. Pat. No. 6,068, 623, U.S. Pat. No. 6,228,072, and copending applications entitled FLEXIBLE CATHETER, application Ser. No. 09/253,591, filed Feb. 22, 1999, and FLEXIBLE CATHETER WITH BALLOON SEAL BANDS, application Ser. No. 09/653,217, filed Aug. 31, 2000, all of which are hereby incorporated by reference in their entirety. One preferred guidewire system is available from Medtronic PercuSurge, Inc. of Sunnyvale, Calif., under the name GUARDWIRE PLUS™.

As illustrated in FIG. 2A, an occlusive device such as an inflatable balloon 12 is mounted on the distal end 48 of tubular body 44. In one preferred embodiment, the balloon 12 is a compliant balloon formed of a material comprising a block polymer of styrene-ethylene-butylene-styrene (SEBS), as disclosed in assignee's copending application entitled BALLOON CATHETER AND METHOD OF MANUFACTURE, application Ser. No. 09/026,225, filed on Feb. 19, 1998, and in U.S. Pat. No. 5,868,705, the entirety of both of which are hereby incorporated by reference. The balloon 12 may be secured to the tubular body 44 by any means known to those skilled in the art, such as adhesives or heat bonding. For example, for attachment of a SEBS balloon to a nitinol tube, a primer such as 7701 LOCTITE™ by Loctite Corporation is preferably used along with cyanoacrylate adhesive such as LOCTITE-4011.

The balloon 12 described in the preferred embodiments preferably has a length of about 5 to 9 mm and more preferably about 6 to 8 mm. Other occlusive devices such as filters are suitable for the catheter 44, such as those disclosed in assignee's copending applications entitled OCCLUSION OF A VESSEL, Ser. No. 09/026,106, filed Feb. 19, 1998, OCCLUSION OF A VESSEL, Ser. No. 09/374,741, filed Aug. 13, 1999, OCCLUSION OF A VESSEL AND ADAPTER THEREFOR, Ser. No. 09/509,911, filed Feb. 17, 2000, MEMBRANES FOR OCCLUSION DEVICE AND METHODS AND APPARATUS FOR REDUCING CLOGGING, Ser. No. 09/505,554, filed Feb. 17, 2000, and STRUT DESIGN FOR AN OCCLUSION DEVICE, Ser. No. 09/505,546, filed Feb. 17, 2000, the entirety of each of which is hereby incorporated by reference.

With reference to FIG. 2B, a core wire 54 is provided inside the lumen 50 and is crimped to the tubular body 44. Coils 56 extend from the distal end of the tubular body 44, surround the core wire 54, and terminate in a distal ball 58. In one embodiment, the core wire may have one or more tapers, and can extend proximally into tubular body 44. Other details regarding the core wire are discussed in assignee's copending application entitled CATHETER CORE WIRE, Ser. No. 09/253,971, filed Feb. 22, 1999, the entirety of which is hereby incorporated by reference.

In one embodiment, shown in FIG. 2B, the tubular body 44 preferably has cuts 60 to create a coiled configuration. A sleeve 62 is preferably provided over the tubular body 44. Adhesive stops 64 and 66 are provided about 1 to 2 mm from the ends of the balloon, to control the wicking length of the adhesive 68 into the balloon working area. Balloon inflation is provided through the cuts 60 in the tubular body 44. A marker 70 is mounted to the tubular body 66 proximal of the balloon 12. Adhesive tapers 72 and 74 are provided adjacent the balloon 12 to provide a transition region between the tubular body 44 and balloon 12 at the balloon's proximal end and between the balloon 12 and the core wire 54 at the balloon's distal end. Seal bands 76 and 78 are applied to the proximal and distal ends of the balloon to improve bond integrity. Other details regarding this balloon catheter may be found in assignee's above-referenced copending applications entitled FLEXIBLE CATHETER and FLEXIBLE CATHETER WITH BALLOON SEAL BANDS.

D. Inflation Adapter and Low Profile Catheter Valve

Figure 3:
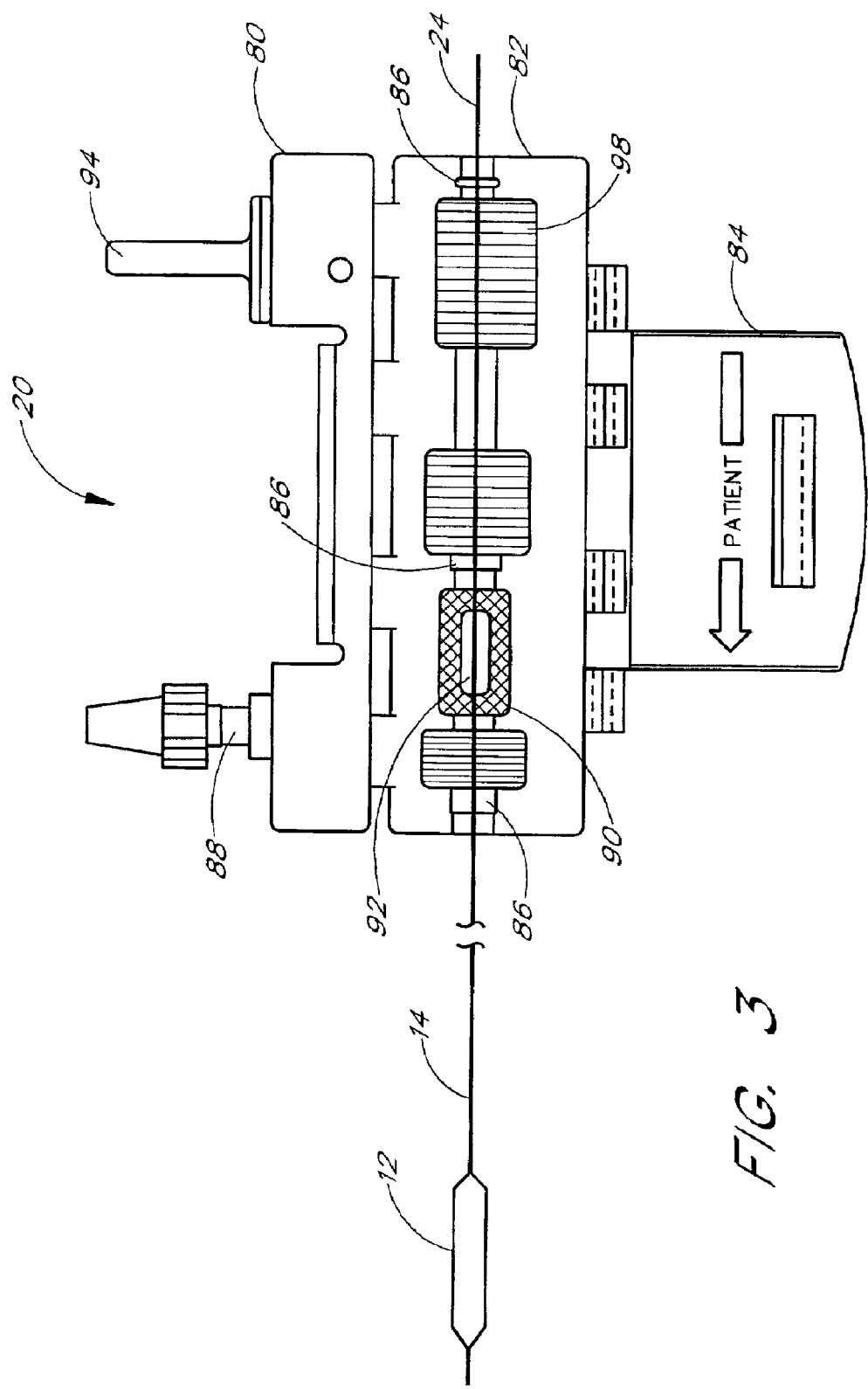
FIG. 3 shows the inflation adapter of FIG. 1 having a low profile catheter valve and balloon catheter placed therewithin.

Referring next to FIG. 3, the inflation adapter 20 comprises a housing having two halves 80, 82 preferably formed of metal, medical grade polycarbonate, or the like. The halves 80, 82 are attached by hinges to be separated or joined in a clam shell manner. A locking clip 84 secures the halves while the adapter 20 is in use. Clips 82 within the housing accept and securely hold the catheter 14 in a correct position.

The male luer member 88 or another suitable connector, extends from a top of the housing to provide an inflation passageway. Seals 90 are provided within the housing and around an internal segment 92 of the inflation pathway to conduct the pressurized fluid provided by the syringe assembly 22. An actuator 94, shown in FIG. 1 at the top of the adapter housing 96, controls a cam which operates sliding panels 98 (FIG. 3) contained in the housing.

As shown in FIG. 1, a low profile catheter valve 24 is attached to an open proximal end of the catheter 14. Inflation fluid is injected through the adapter 20 and valve 24 into a lumen of the hollow catheter 14, and into the balloon 12. The inflation adapter 20 is used to open and close the valve 24 to regulate the inflation of the balloon 12 mounted on the distal end of the catheter 14.

It will be emphasized that other types of adapters and/or valves can be employed with the inflation syringe and/or syringe assembly described herein, in order to achieve rapid and accurate inflation/deflation of medical balloons or other non-balloon medical devices. Therefore, although the preferred embodiments are illustrated in connection with a low volume occlusion balloon 12, other types of balloons and non-balloon devices can benefit from the advantages of the invention described herein.

As shown in FIGS. 4A and 4B, the low profile catheter valve 24 comprises a movable sealer portion 100 attached at a distal end of a wire segment 102 and positioned within the inflation lumen 50 of the guidewire catheter 14. The wire 102 may be secured to a spring just within a proximal opening of the catheter 14. It will be noted that various spring or biasing arrangements may be utilized, including a zig-zag wire 104 which is formed on or replaces the wire segment 102 and which provides biasing force to the sealer portion 100 due to frictional engagement with the walls of the lumen 50. The sealer portion 100 forms a fluid tight seal with the inflation lumen 50 by firmly contacting the entire circumference of a section of the inflation lumen 50. The sealer portion 100 may be positioned proximally of the side-access inflation port 90 on the catheter as shown in FIG. 4B, to establish an unrestricted fluid pathway between the inflation port 52 and the inflatable balloon on the distal end. As desired, the clinician may move the sealer portion 100 to a position at or distal of the inflation port 52, as shown in phantom in FIG. 4B, thereby preventing any fluid from being introduced into or withdrawn from the lumen 50 via the inflation port 52. The valve 24 is considered "low profile" because it is no larger in cross-sectional diameter than the catheter 14 itself.

Preferably, the catheter 14 is positioned within the housing of the adapter 20 with the valve closed, such that the side inflation port 52 is located in the sealed inflation area 92 of the housing. The catheter 14 is then positioned in the second half 82 of the adapter 20. A distal portion of the catheter 14 extends out of the housing and into the patient, and a proximal portion of the catheter including the catheter valve 24 extends out of the other side of the adapter 20. The adapter is closed, the locking clip 84 is secured, and a syringe assembly is attached. The actuator 94 is moved from a first position to a second position, such that the sliding panels 98 within the housing cause the valve 24 to be in an open position to allow fluid flow through the inflation port 52. A syringe assembly 22 is then used to inflate the balloon 12. Closing the valve 24 is accomplished by moving the actuator 96 from the second position back to the first position, such that the balloon inflation is maintained. Once the valve is closed the adapter may be removed and treatment and other catheters may be delivered over the guidewire.

Other inflation adapter/inflation syringe assemblies may also be used. Also, the adapter 20 can have additional features, such as a safety lock provided on the actuator knob 94 to prevent accidental opening when the adapter is being used and the catheter valve is open. In addition, the adapter can be provided with an overdrive system to overdrive a sealing member into a catheter. Details of these features and other inflation assemblies may be found in assignee's U.S. Pat. No. 6,050,972 and copending applications, SYRINGE AND METHOD FOR INFLATING LOW PROFILE CATHETER BALLOONS, application Ser. No. 09/025,991, filed Feb. 19, 1998, and LOW VOLUME SYRINGE AND METHOD FOR INFLATING SURGICAL BALLOONS, application Ser. No. 09/195,796, filed Nov. 19, 1998, all of which are incorporated by reference in their entirety.

E. Aspiration Catheter

The occlusion system described above advantageously enables an exchange of catheters over a guidewire while an occlusive device isolates particles within the blood vessel. For example, a therapy catheter can be delivered over the guidewire to perform treatment, and then be exchanged with an aspiration catheter to remove particles from the vessel. Further details of this exchange are described in assignee's copending application entitled EXCHANGE METHOD FOR EMBOLI CONTAINMENT, Ser. No. 09/049,712, filed Mar. 27, 1998, the entirety of which is hereby incorporated by reference.

Figure 5:
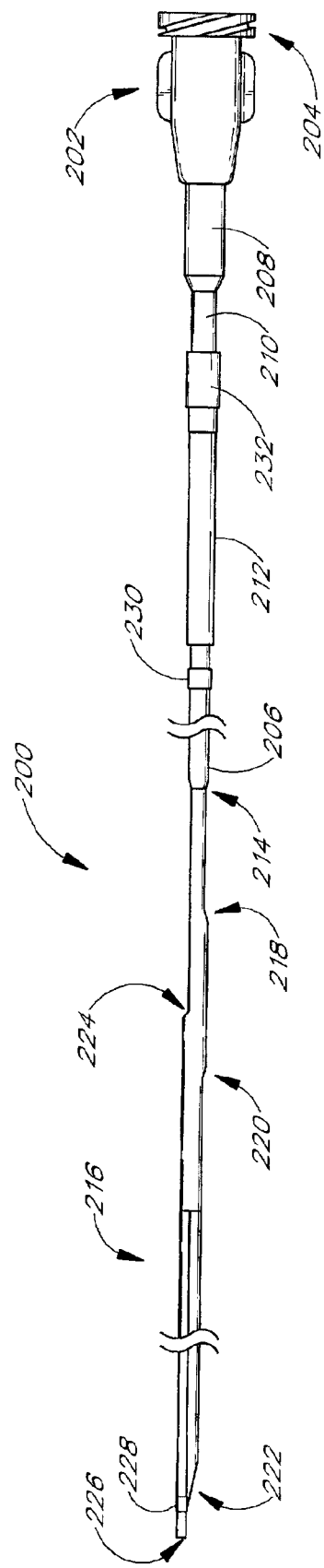
FIG. 5 is a side view of an illustrative single operator type aspiration catheter according to a preferred embodiment of the present invention.

An aspiration catheter according to one preferred embodiment of the present invention is shown in FIG. 5. The catheter 200 includes an adapter 202 and an aspiration port 204 at its proximal end to which a source of negative pressure is attached. The aspiration catheter further comprises an elongate tubular body 206 which extends distally from the adapter 202 and through a plurality of support sheaths 210 and 212. Beyond the support sheath 212 the elongate tubular body 206 extends to a transition point 214 where the outer diameter of the tubular body 206 tapers down in size. This tapered or necked-down portion of the tubular body 206 is preferably inserted into a dual lumen tubing 216 through the proximal end 218 of the dual lumen tubing. The tubular body 206 is preferably inserted into one of the lumens of the dual lumen tubing 216 such that its distal end 220 is a sufficient distance distal from the proximal end 218 of the dual lumen tubing to provide a secure connection therebetween.

The dual lumen tubing 216 preferably defines two lumens, one for aspiration and the other for a guidewire to pass therethrough. More particularly, the lumen that the elongate body 206 is inserted into acts as the aspiration lumen, being in fluid communication with the lumen of the elongate tubular body 206. The aspiration lumen preferably ends in a distal aspiration mouth 222, which preferably defines an oblique opening. Aspiration therefore occurs through both the lumen of the elongate tubular body 206 and the aspiration lumen of the dual lumen tubing.

The guidewire lumen is provided adjacent the aspiration lumen in the dual lumen tubing and has a proximal end 224 preferably distal to the proximal end 218 of the aspiration lumen of the dual lumen tubing, and a distal end 226 preferably distal to the aspiration mouth 222. A marker 228 is placed within the guidewire lumen at the distal end of the aspiration mouth. Additional markers 230, 232 may also be placed over the elongate body 206 and/or support sheaths. Further details regarding these and other aspiration catheters are provided below and in Applicant's copending applications entitled ASPIRATION CATHETER, Ser. No. 09/454, 522, filed Dec. 7, 1999, and U.S. Pat. No. 6,152,909, the entirety of both of which are hereby incorporated by reference.

II. Drug Delivery and Other Treatment Methods

In a preferred embodiment of the invention, an occlusion balloon guidewire 14 such as described above is delivered to the site of an occlusion in a blood vessel. In one embodiment (not shown), a guide catheter is first introduced into the patient's vasculature through an incision made in the femoral artery in the groin and is used to guide the insertion of the guidewire and/or other catheters and devices to the desired site. The guidewire is then advanced until its distal end reaches a site proximal to the occlusion. Fluoroscopy is typically used to guide the guidewire and other devices to the desired location within the patient. The devices are frequently marked with radiopaque markings to facilitate visualization of the insertion and positioning of the devices within the patient's vasculature. It should be noted that at this point, blood is flowing through the vessel in a proximal to distal direction. The guide catheter may then be removed, or alternatively, may be used as the aspiration catheter itself, as described below.

A. Aspirating While Crossing the Occlusion

In one embodiment, aspiration is performed while advancing a guidewire across the site of the occlusion in a proximal to distal direction to prevent distal embolization. An aspiration catheter, such as described below, is delivered over the guidewire to a site just proximal to the site of the occlusion, and, while aspirating, the occlusion in the vessel is crossed with both the guidewire and the aspiration catheter in a proximal to distal direction. Further details of this method are described in assignee's copending application entitled METHODS FOR REDUCING DISTAL EMBOLIZATION, Ser. No. 09/438,030, filed Nov. 10, 1999, and in U.S. Pat. No. 5,833,650, the entirety of both of which are hereby incorporated by reference. The term "aspiration catheter" is intended to include any elongated body having a lumen which can be used to withdraw particles, fluid or other materials from a blood vessel. Any such device can be attached to a suction apparatus for removal of intravascular particles.

Figure 6A:
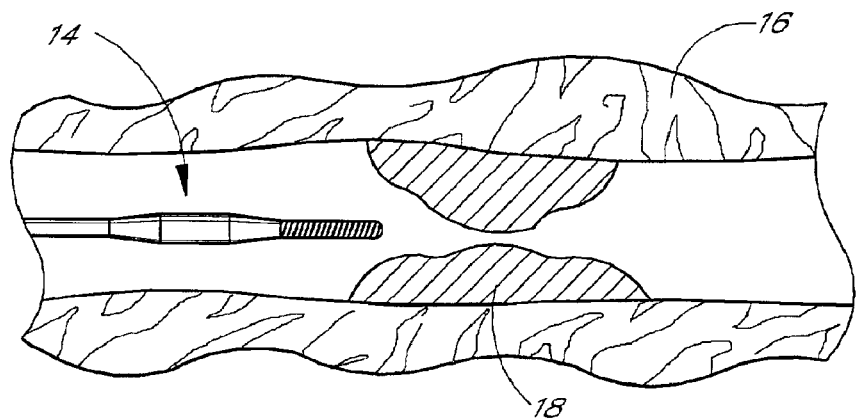
FIGS. 6A–6D are partial cross-sectional views of a guidewire having an occlusion balloon and an aspiration catheter crossing an occlusion.
Figure 6B:
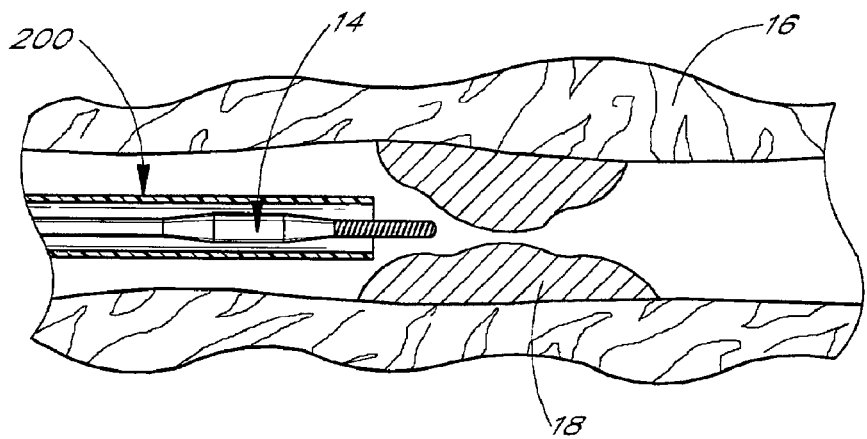
Figure 6C:
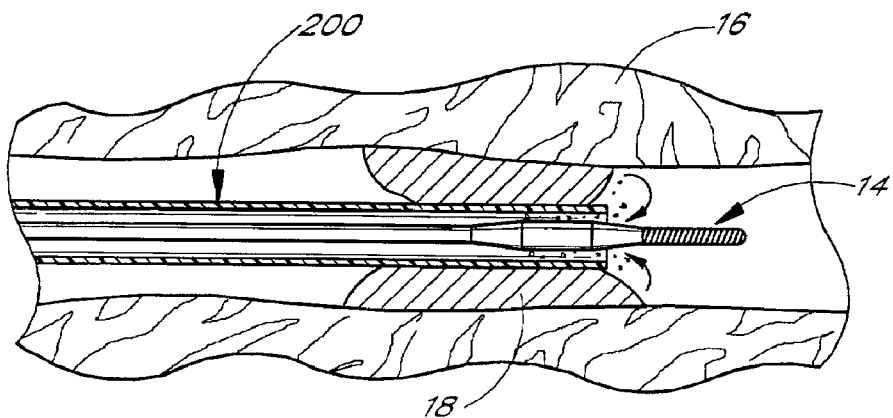
Figure 6D:
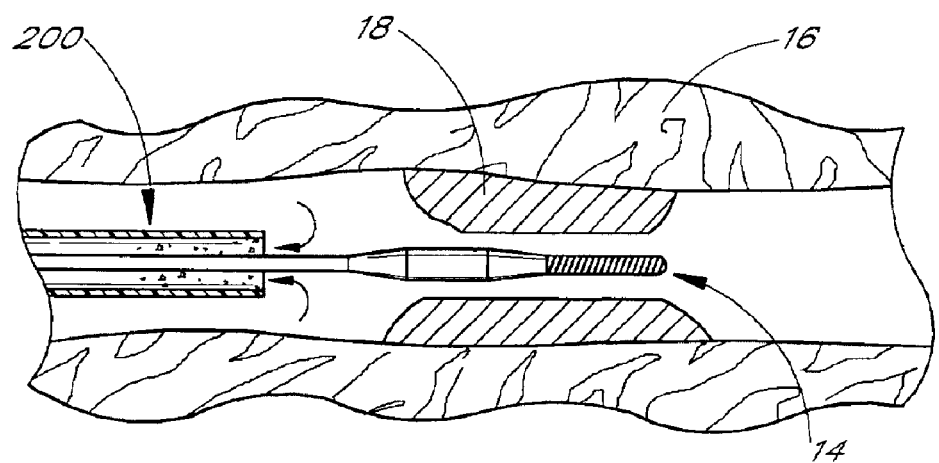

FIGS. 6A–6D illustrate one embodiment in which an occlusion 18 in a vessel 16 is crossed with a guidewire having an occlusive device and an illustrative aspiration catheter 200. It will be appreciated, however, that the occlusion 18 may first be crossed with an ordinary guidewire as described in the above-referenced application METHODS FOR REDUCING DISTAL EMBOLIZATION. A guidewire 14 with an occlusive device such as a balloon at its distal end is inserted into the vessel 16 to a location just proximal to the occlusion 18 (FIG. 6A). An aspiration catheter 200 is delivered over the guidewire 14 so that the distal ends of the guidewire 14 and aspiration catheter 200 are both just proximal to the occlusion 18 (FIG. 6B). Alternatively, the aspiration catheter can be delivered first. Aspiration is performed while crossing or advancing past the occlusion 18 with the distal ends of the guidewire 14 and aspiration catheter 200, in a proximal to distal direction (FIG. 6C). Then the distal end of the aspiration catheter 200 is moved back in a distal to proximal direction while aspirating (FIG. 6D). Blood flow into the aspiration catheter 200 is indicated by the arrows. The proximal to distal, then distal to proximal aspiration may be repeated one or more times if desired.

In one embodiment, the distal tip of the aspiration catheter is no more than about 2 cm, in another embodiment no more than about 0.5–1 cm, behind or proximal to the distal tip of the guidewire during crossing. In yet another embodiment, the distal end of the aspiration catheter is then moved in a distal to proximal direction across the occlusion, while continuously aspirating. This process ensures the removal of any particles which may be created during the delivery of the guidewire to a position distal to at least a portion of the occlusion. Aspiration from proximal to distal, and distal to proximal, can be repeated as many times as necessary to completely aspirate all particles. These procedures are all preferably performed prior to occlusion of the vessel at a site distal to the occlusion with the occlusion device, and prior to treatment of the occlusion. It should be noted that, as used herein, "proximal" refers to the portion of the apparatus closest to the end which remains outside the patient's body, and "distal" refers to the portion closest to the end inserted into the patient's body.

As the guidewire and aspiration catheter cross the occlusion, blood and/or other fluid enters the vessel and keeps any particles dislodged during the procedure from flowing in a distal to proximal direction. In addition, the blood pressure and flow provides the irrigation necessary for aspiration. The blood pressure in the vessel is preferably at least about 0.2 psi, and the vessel is capable of providing a flow rate of at least about 5 cc per minute when not occluded.

B. Drug Delivery

In a drug or fluid delivery embodiment of the present invention, after the distal end of the guidewire having an occlusive device such as a balloon or filter is delivered past the site of the occlusion and the optional aspiration step is complete, the occlusive device is actuated to at least partially, and in one embodiment totally, occlude the vessel at a site distal to the site of the occlusion. In another embodiment, prior to actuation of the occlusive device, a first therapy or other catheter is delivered over the guidewire. Once the blood vessel is occluded, therapy can be performed by delivering a drug or fluid through a catheter advanced over the guidewire to the site of the occlusion as described herein to partially or totally dissolve the occlusion. After therapy has been performed, aspiration of any particles broken off from the occlusion may also be performed while the occlusive device is actuated. It will be appreciated that it may take time for the drug to dissolve or act on the occlusion, and therefore a clinician may wait a desired period before aspirating.

Various thrombolytic or other types of drugs can be delivered locally in high concentrations to the site of the occlusion via a therapy catheter. It is also possible to deliver various chemical substances or enzymes via a therapy catheter to the site of the stenosis to dissolve the obstruction. The therapy catheter can be any of a number of devices that may or may not ride over the guidewire, including a balloon catheter used to perform angioplasty, a catheter which delivers a stent, an atherectomy device, a laser or ultrasound device used to ablate the occlusion and similar devices. Drug delivery using a therapy catheter is shown in FIG. 7.

Figure 7:
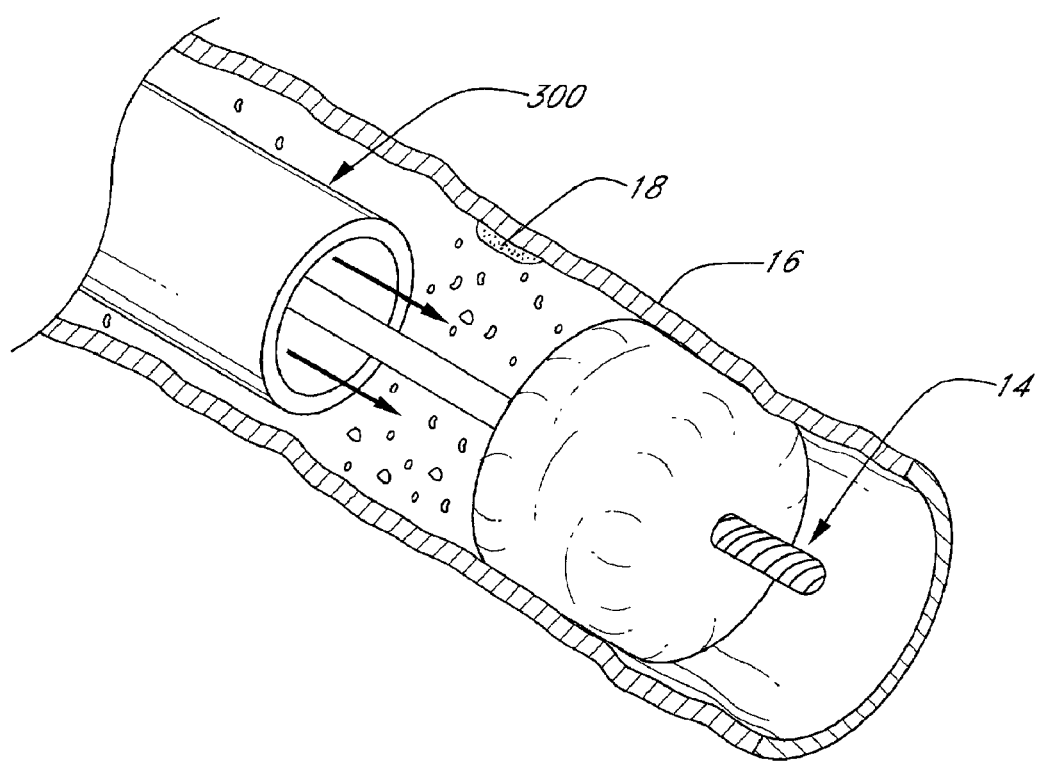
FIG. 7 is a perspective view of a therapy catheter delivering a drug and a guidewire having an occlusive device inserted into a blood vessel, with the blood vessel shown partially cut away.

Referring to FIG. 7, once the vessel 16 is occluded with the occlusion guidewire 14, a therapy catheter 300 is used to treat the occlusion 18. The therapy catheter can be any of a number of devices, including a balloon catheter used to perform angioplasty, a catheter which delivers a stent, a catheter for delivering enzymes, chemicals, or drugs to dissolve and treat the occlusion (as illustrated in FIG. 7), an atherectomy device, or a laser or ultrasound device used to ablate the occlusion. Alternatively, the therapy catheter can be eliminated and use of the guide catheter or a separate aspiration catheter alone can be used to aspirate the occlusion. This method is especially useful to remove emboli from the coronary arteries or saphenous vein graft following acute myocardial infarction, because the aspiration catheter can be made small enough to enter the coronary arteries.

Figure 8A:
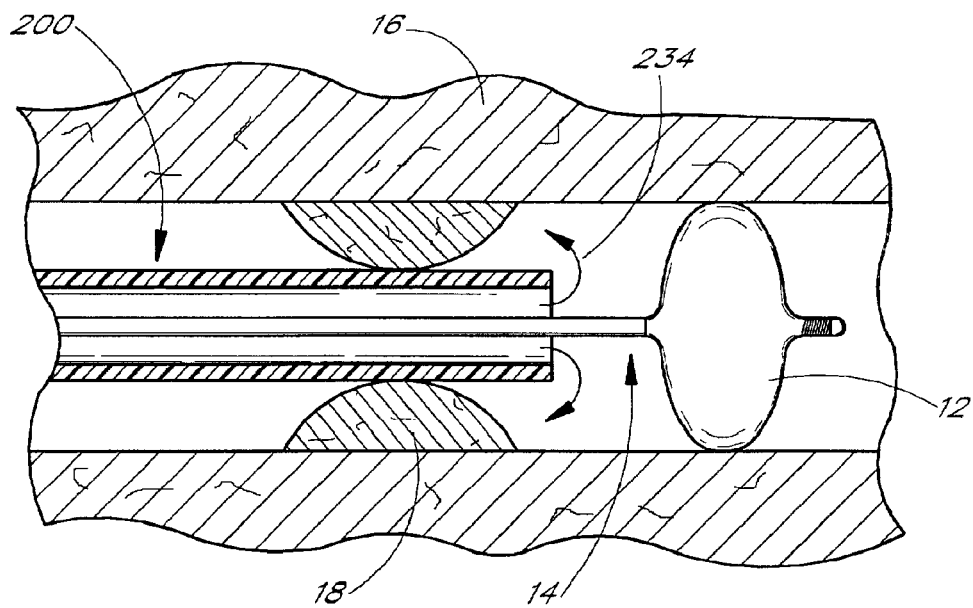
FIGS. 8A and 8B show a catheter having an occlusive device at its distal end, and an aspiration catheter, inserted into a blood vessel to treat an intravascular occlusion using the drug delivery method according to one embodiment of the present invention.
Figure 8B:
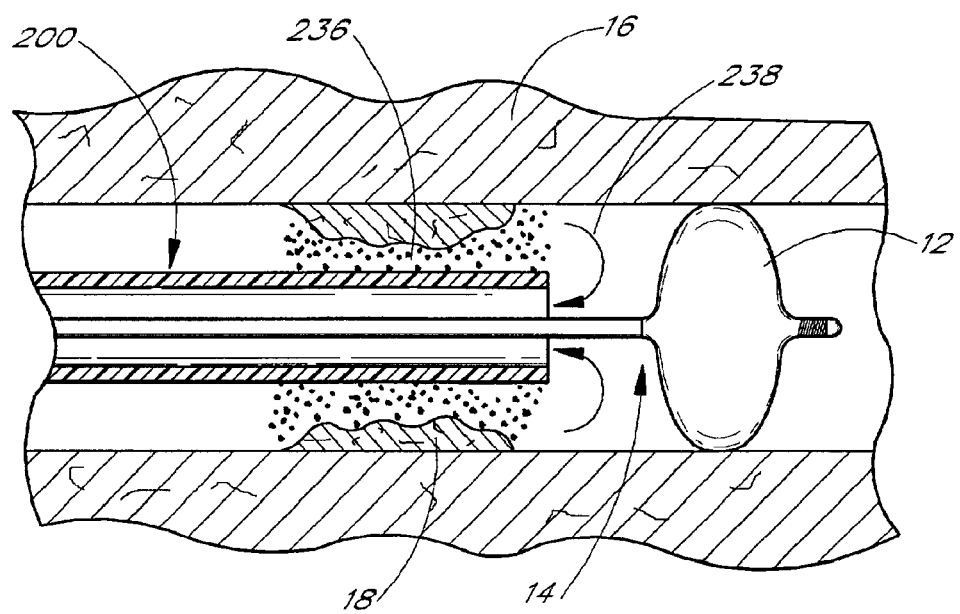

Thus, as illustrated in FIGS. 8A and 8B, in one embodiment, both therapy and aspiration are preferably performed using the same catheter, which is preferably an aspiration catheter 200. Although aspiration catheter 200 as shown in FIGS. 8A and 8B has only one lumen, it will be appreciated that other types of aspiration catheters may be used. For example, an aspiration catheter such as described in FIG. 5 can be employed. Other aspiration catheters are described in U.S. Pat. No. 6,152,909.

In the embodiment where an aspiration catheter 200 aspirates while the guidewire 14 crosses the occlusion 18 as described above, when the occlusive device is actuated the aspiration catheter is already delivered to the site of the occlusion over the guidewire. It will also be appreciated, however, that the guidewire 14 may cross the occlusion 18 without aspirating simultaneously. In this embodiment, the aspiration catheter 200 may be delivered after the guidewire crosses the occlusion. The aspiration catheter is then preferably delivered until it is proximal to the occlusion 18 before the occlusive device such as a balloon is actuated. By actuating the occlusive device before the aspiration catheter crosses the occlusion, the risk of particles migrating downstream during crossing of the occlusion by the aspiration catheter is eliminated. Alternatively, if there is minimal risk that the crossing of the aspiration catheter will break off particles, the occlusive device can be actuated after the aspiration catheter crosses the occlusion 18. As shown in FIG. 8A, once delivered, aspiration catheter 200 is preferably proximal to the balloon 12 and distal to the occlusion 18.

One embodiment relates to localized delivery of high concentrations of a thrombolytic, anticoagulant or restenosis-inhibiting drug through the lumen of the aspiration catheter, to promote dissolution of the occlusion and restoration of blood flow through the blood vessel. The fluid containing the drug which is delivered from the aspiration catheter travels in a proximal to distal direction out of the lumen of the aspiration catheter, as indicated by arrows 234 in FIG. 8A, and then in a distal to proximal direction after contacting the occlusive device, and displaces blood proximally. Additionally, blood flow in the vessel in a proximal to distal direction localizes the drug containing fluid to the area of the occlusion.

Thrombolytic agents contemplated for use in the preferred embodiments of the present invention include, but are not limited to, tissue plasminogen activator (t-PA), streptokinase. Anticoagulants include heparin, hirudin and coumadin. In addition, solutions such as phosphate-buffered saline (PBS), lactated Ringer's solution, or any other pharmaceutically acceptable solution may be used to deliver a radioisotope to the site of an occlusion which has been treated with a therapy catheter to inhibit restenosis of the occlusion. These radioisotopes, including beta-emitters (e.g., $^{32}$P) and gamma-emitters (e.g., $^{131}$I), and any other medically acceptable radioisotopes well known in the art, permanently damage the treated occlusion and prevent tissue regrowth.

Other therapeutic or other agents that may be used include, but are not limited to, thrombin inhibitors, anti-thrombogenic agents, fibrinolytic agents, cytostatic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, antimetabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

In one embodiment, the drug is delivered through the lumen of the aspiration catheter at a flow rate of between about 0.1 cc/sec and 10 cc/sec, in another embodiment, about 0.5 to 2 cc/sec, and in yet another embodiment, about 0.5 cc/sec to 1 cc/sec. In another embodiment, the tip of the aspiration catheter is placed about 0.5 mm to 10 mm, more preferably about 1 mm to 5 mm, from the surface of the occlusive device. Localization of the tip of the aspiration catheter close to the occlusive device 12 creates a more isolated area for drug treatment of the occlusion. In one embodiment, when the tip of the aspiration catheter is close to the surface of the occlusive device, the fluid containing the drug replaces the column of blood distal to the catheter tip, resulting in proximal to distal movement of the fluid containing the drug which replaces the column of blood distal to the catheter tip. In contrast, if the tip of the catheter is placed too far proximal to the occlusive device, the fluid containing the drug cannot move forward out of the catheter due to the force exerted by the column of blood distal to the catheter tip.

In another embodiment, when the drug delivered through the lumen of the aspiration catheter is released at a rapid rate, the drug moves in a proximal to distal direction toward the occlusive device. Once the drug reaches the occlusive device, at least a portion of the drug bounces against the occlusive device and moves in a distal to proximal direction. This localizes the drug at a location proximal to the occlusive device.

After drugs are delivered through the aspiration catheter 200, emboli or other particles 236 may be formed in the vessel as shown in FIG. 8B. Aspiration can then occur through the same lumen that delivered drugs to the occlusion 18, as indicated by arrows 238. The aspiration catheter may preferably be moved proximally and distally in order to optimize aspiration. The use of the same aspiration catheter lumen advantageously reduces the time that the occlusive device remains expanded, thereby minimizing risk to the patient. Once aspiration is complete, the occlusive device can be deactivated to restore blood flow to the vessel. Further details regarding aspirating particles are described in U.S. Pat. No. 6,135,992, the entirety of which is incorporated by reference. Following aspiration, additional therapy can be performed using a therapy catheter if desired. When separate therapy and aspiration catheters are used, once the desired therapy is performed, the therapy catheter is withdrawn from the patient's body and the aspiration catheter can once again be delivered over the guidewire.

The aspiration catheter, as shown in FIGS. 8A and 8B, rides over the guidewire with the guidewire inserted through the aspiration lumen of the catheter. Alternatively, a single operator type aspiration catheter can be used, in which only a portion of the aspiration catheter rides over the guidewire, which is inserted into a separate guidewire lumen. Single operator catheters suitable for use with these embodiments are described below.

C. Irrigation Catheters

Figure 9A:
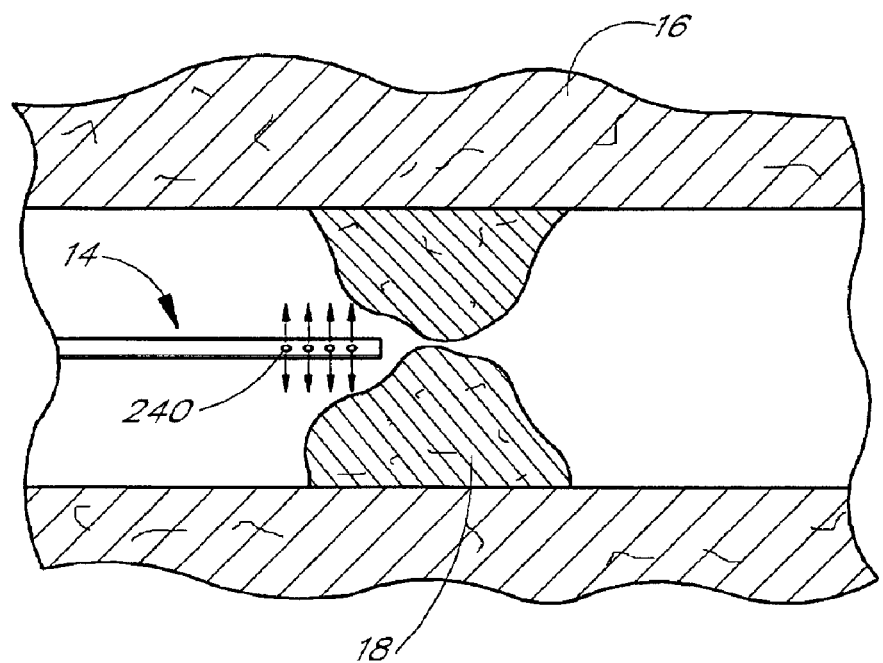
FIG. 9A is a side view of a guidewire having side ports for delivering fluids to an occlusion in a blood vessel, with the vessel shown partially cut away.
Figure 9B:
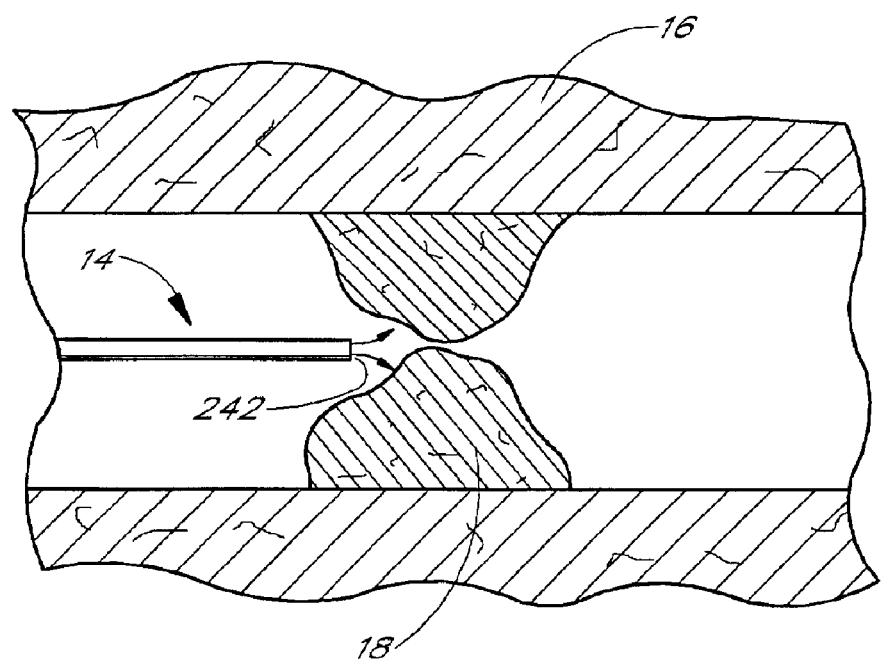
FIG. 9B is a side view of a guidewire having an irrigation hole at its distal end for delivering fluids to an occlusion in a blood vessel, with the vessel shown partially cut away.

It will be appreciated that when the occlusion in the vessel is too large, it is often desirable to create some space to move past the occlusion prior to delivering the guidewire 14 having the occlusive device. To do this, a guidewire 14 without a balloon or other occlusive device may be used which contains side ports 240 near the distal end and/or an irrigation hole 242 at its distal end, as shown in FIGS. 9A and 9B, respectively. Fluids such as described above are ejected through these holes to break apart the occlusion as the guidewire crosses the occlusion. Further details describing guidewires for fluid delivery are contained in assignee's U.S. Pat. No. 6,068,623. After the guidewire has cleared space through the occlusion, in one embodiment a therapy catheter or aspiration catheter as described above can simply be delivered over this catheter to perform treatment on the occlusion. It will also be appreciated that an aspiration catheter may simultaneously be used to aspirate particles broken off from the occlusion while the guidewire shown in FIGS. 9A and 9B crosses the occlusion, such as described above.

In another embodiment, after the guidewire has cleared some space, the guidewire is exchanged for a guidewire having an occlusive device as described above. Further details regarding this type of exchange are described in U.S. Pat. No. 6,159,195, the entirety of which is hereby incorporated by reference. In addition, if an aspiration catheter is already provided on the guidewire, the aspiration catheter itself may be used for the exchange.

Once the guidewire having an occlusive device is delivered, the vessel is then treated such as described above. For instance, an aspiration catheter may be used as described above to deliver drugs to dissolve the occlusion, followed by aspiration. These procedures preferably occur while the balloon on the catheter is inflated. The aspiration catheter is then removed and, optionally, the therapy catheter is inserted to perform therapy, the therapy catheter is removed and the aspiration catheter is delivered to aspirate the particles resulting from the therapy.

Figure 10A:
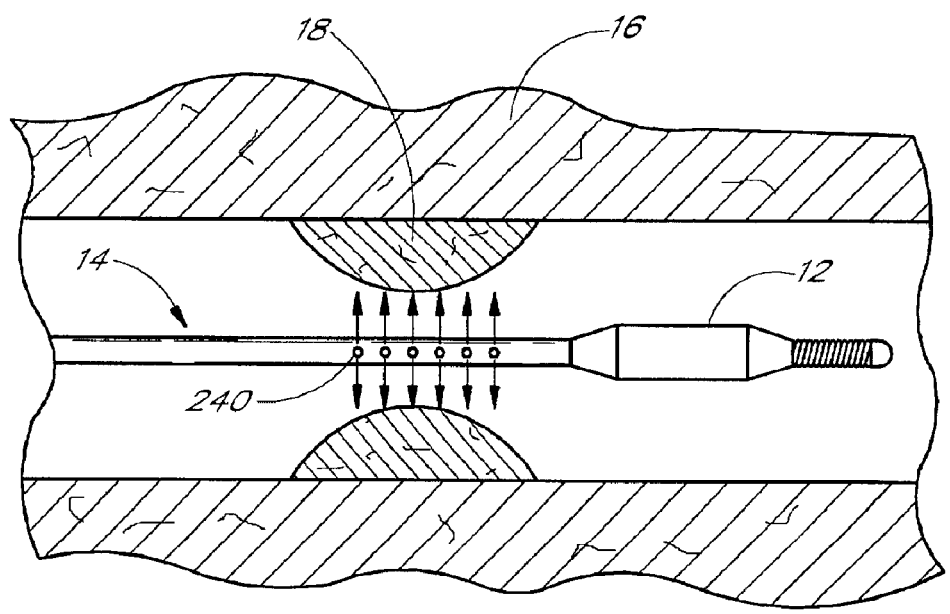
FIG. 10A is a side view of a temporary occlusion balloon catheter having side ports for delivering fluids to an occlusion in the blood vessel, with the vessel shown partially cut away.
Figure 10B:
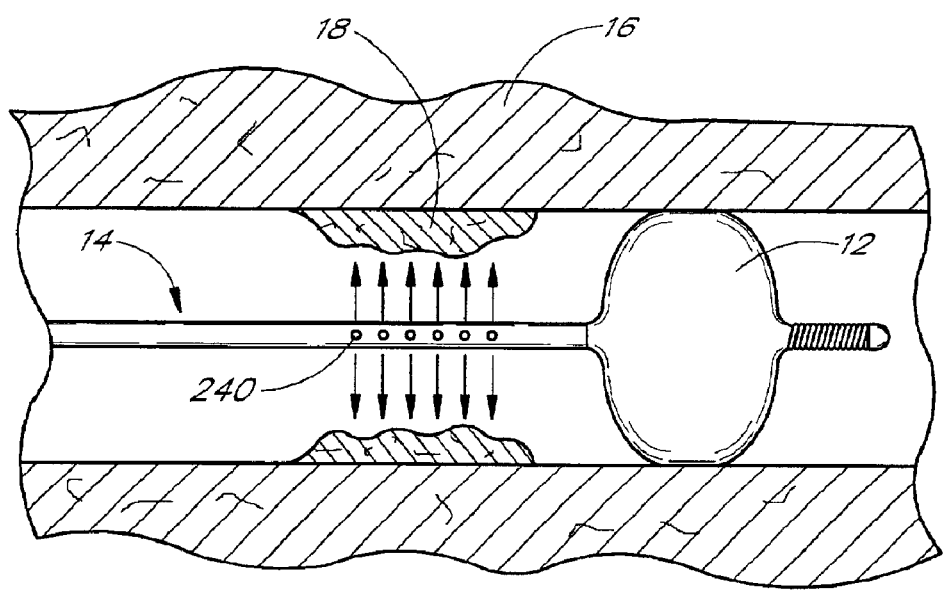
FIG. 10B is a side view of the catheter of FIG. 10A, showing the balloon inflated.

In another embodiment shown in FIG. 10A, a temporary occlusion balloon catheter 14 is delivered which contains irrigation holes 240 proximal to the balloon 12. These holes allow for the ejection of drugs to dissolve the occlusion 18 as the guidewire passes therethrough. Additionally, the same fluid used for drug delivery may also be the fluid used for balloon inflation. Drugs may be delivered both while the guidewire crosses the occlusion, and also while the balloon 12 on the guidewire 14 is inflated, shown in FIG. 10B. An aspiration catheter as described above may be used to aspirate particles while the guidewire crosses the occlusion and also while the balloon is inflated and drugs are delivered through the holes 240 in the guidewire FIGS. 11A–11C illustrate other irrigation catheters for use with the above embodiments that provide a nitinol hollow guidewire having the capability to pass fluid therethrough. FIG. 11A illustrates a preferred embodiment of an irrigation catheter 302A constructed from a superelastic nitinol hollow wire. In this embodiment, the irrigation catheter 302A is comprised of an hypotube 304 and a coil member 306. The hypotube 304 is provided with proximal and distal ends 308 and 310 as well as a lumen 312 extending along the hypotube 304, thereby providing a fluid passageway. The coil member 306 of the catheter 302A is joined to the distal end 310 of the hypotube 304 as in the manner shown in FIG. 11A. The distal end 310 of the hypotube 304 may also include one or more perforations 314 thereof so that fluids can be delivered into or received from the desired body locations. In addition to distal perforations 314, gaps between the coil turns 316 also provide an effective passageway to deliver or receive fluids through coil member 306. Therefore, in this embodiment, perforations 314 at the distal end 310 of the hypotube 304 are optional so that the fluid may exit or enter the catheter 302A from the coil member 306. Although the catheter 302A of this embodiment can be used for delivering drugs to the distal body locations, the catheter 302A can also be used in those applications where irrigation and aspiration are necessary for emboli removal. For the most available cardiovascular catheters, the outer diameter of this irrigation catheter is about 0.38" or smaller.

FIG. 11B shows a second embodiment which comprises a multilumen irrigation catheter 302B. In this embodiment, a portion of the catheter 302B comprising the hypotube 304 and the coil member 306 is configured similar to that of first embodiment. As a departure from the previous embodiment, however, the present embodiment also comprises a balloon member 318 and a conduit 320. The conduit 320 is preferably disposed along the inner lumen 312 of the hypotube 304. The balloon member 318 is coaxially mounted on the distal end 310 of the hypotube 304 as in the manner shown in FIG. 11B. The conduit 320 is provided with distal and proximal ends 322 and 324 as well as an inner lumen 326.

In this embodiment, the proximal end 322 of the conduit 320 is preferably connected to a gas source (not shown), while the distal end 324 is connected to the balloon member 318 through an inlet port 328 in the distal end 310 of the hypotube 304. The distal end 324 of the conduit 320 and the inlet port 328 are sealably connected to each other by suitable means such as adhesive to avoid any gas leak. In this arrangement, the inner lumen 326 of the conduit 320 connects the gas source to the balloon member 318 so that the gas from the gas source can inflate the balloon member 318.

The conduit 320 is preferably made of a flexible material such as polyimide, polyamide, or the like alloy and is in the form of hypotubing. Preferably, the outer diameter of the conduit 320 is significantly smaller than the inner diameter of the lumen 312 of the hypotube 304 so that fluid in the lumen 312 can flow without any restriction. In this embodiment, carbon dioxide ($CO_2$) gas is preferably employed to inflate balloon member 318. In fact, ($CO_2$) gas easily dissolves in blood and does not cause any harm in the patient's body, if an accidental leak occurs. If desired, however, the balloon member may be inflated using any of a number of harmless gases or fluids, or possible combinations thereof. In applications, the irrigation catheter 302B may function as the catheter 302A in the first embodiment. However, with the inflatable balloon member 318, the catheter 302B can be advantageously used for occlusion and irrigation therapies.

FIG. 11C shows a third embodiment which comprises another single lumen catheter 302C as in the case of first embodiment. In this embodiment, a portion of the catheter 302C comprising the hypotube 304 and the coil member 306 is also configured similar to that of first embodiment. The present embodiment also comprises a balloon member 318. The balloon member 318 is coaxially mounted on the distal end 310 of the hypotube 304 as in the manner shown in FIG. 11B. Fill holes 330 are provided in the wall of the distal end 304 of the hypotube 304 along the section of hypotube enclosed within the balloon member 318. During the application, these fill holes 330 allow the passage of irrigation fluid into the balloon member 318. As the fluid pressure reaches up to inflation pressure of the balloon member 318, the balloon member is inflated. An exemplary inflation pressure range for the occlusion balloons can be given as 40 psi. However, for the therapeutic balloons, such pressure range can be as high as 200 psi.

As shown in FIG. 11C, a number of valve members are also provided over the inner wall of the distal end 310 of the hypotube 304. The valve members are attached over the perforations 85 as in the manner shown in FIG. 11C. Preferably, the valve members 332 are comprised of elastomeric membranes. These membranes 332 can be configured and dimensioned to withstand some threshold fluid pressure, such as the inflation pressure of the balloon member 318.

In application, any pressure over this threshold pressure breaks open these membranes 332, i.e., activates valves 332, and delivers the irrigation fluid, through perforations 314, into the body locations. The fluid delivery can be also provided through leakages from both optional slits (not shown) in the balloon member 318 and the gaps between the coil turns 316. As in the previous embodiment, the catheter 302C can be advantageously used for occlusion and irrigation therapies.

Figure 12:
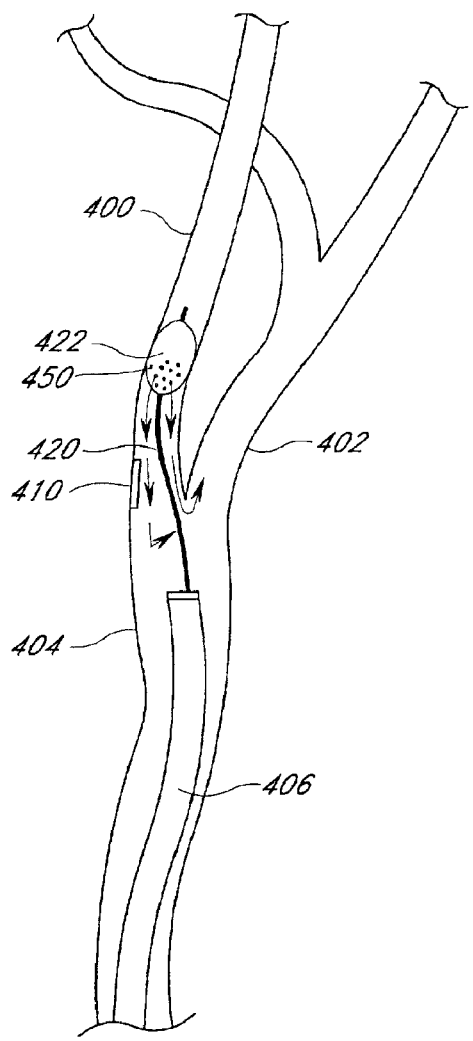
FIG. 12 is a perspective view of an embodiment in which a distal occlusion device has a plurality of holes therein for passing fluid across an occlusion.

FIG. 12 shows another embodiment of an occlusive device capable of passing saline solution, drugs or other fluids across an occlusion. Although this occlusive device is shown for treatment in the carotid arteries, it will be appreciated that the device and method may be used in other locations as well.

A main catheter 406, with or without a distal occlusive device, is introduced into the patient's vasculature through an incision in the femoral artery in the groin of the patient or through direct access to the arteries in the neck. The main catheter 406 is guided through the vasculature until it reaches the common carotid artery 404, where it can remain in place throughout the procedure.

Once the main catheter 406 is in place proximal to the occlusion 410, an inner catheter or guidewire 420 having an occlusive device 422 at its distal end is delivered through the main catheter 406 into the internal carotid artery 400 and past the site of the occlusion 410. Alternatively, a detachable occlusive device can be deployed at the site distal to the occlusion, and the delivery device removed. In this example, the occlusive device 422 is an inflatable balloon. The balloon is inflated to occlude the internal carotid artery 400 at a site distal to the occlusion 410. It should be understood that the occlusion within the artery can be in a discrete location or diffused within the vessel. Therefore, although placement of the distal occlusive device is said to be distal to the occlusion to be treated, portions of the diffuse occlusion may remain distal to the occlusive device.

The occlusive device 422 preferably may be used to flush fluid across the occlusion 410. In one embodiment, the fluid may be saline solution or another suitable flushing solution. In another embodiment, the fluid may be any one of a number of drugs such as described above. The fluid may be advantageously passed through a lumen in the guidewire 420 and into the occlusive device 422. The occlusive device 422 has at least one fluid flow opening and is preferably microporous on its proximal end, having a plurality of holes 450 (e.g., 10–50) that are preferably less than 1000 microns in diameter and more preferably between 50 and 100 microns in diameter. The holes may be formed in the occlusive device 422 by laser drilling, for example. As fluid passes through the occlusive device 422 and into the internal carotid 400, emboli, particulates, and other debris are flushed past the treated occlusion 410 and down the external carotid 402. In embodiments where the occlusion is not formed near the branching of two vessels, the fluid may be isolated across the occlusion as it flows in a proximal direction away from the balloon. Thus, when the fluid used is a drug as described above, the drug is preferably localized across the occlusion for treatment.

Fluid flow may be maintained with a pressurized syringe or other suitable inflation device, as described above, located outside the patient. The fluid is used for inflating the occlusive device 422 as well as for irrigating emboli from the internal carotid 400 down the external carotid 402, or for localizing drugs across the occlusion.

Figure 13:
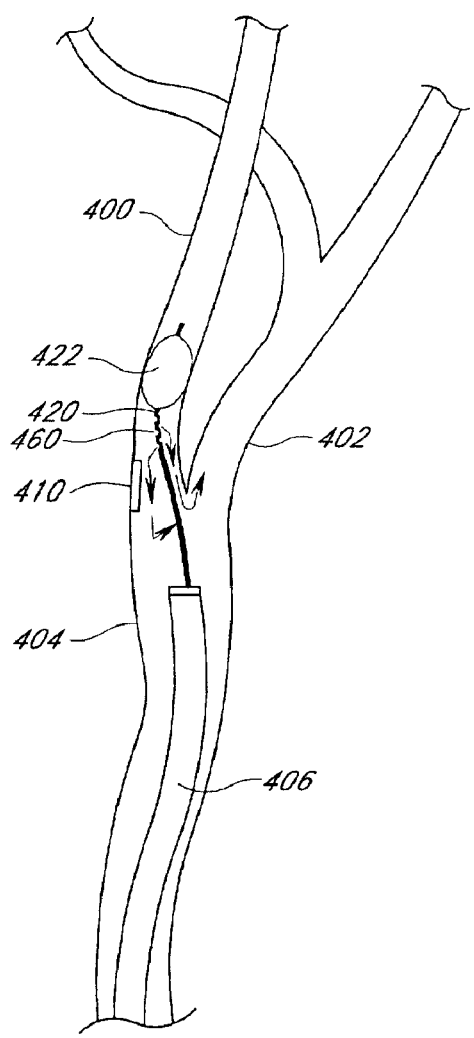
FIG. 13 is a perspective view of an embodiment in which an elongate member (e.g., a guidewire) has a plurality of holes therein for passing fluid across an occlusion.

Another irrigation device and method is disclosed in FIG. 13, in which one or more holes 460 in the guidewire 420 are located distal to the treated lesion 410 and proximal to the occlusive device 422. (For example, 1, 2, or 3 holes of dimensions 0.050"×0.002–0.003" may be used, or 10 holes of dimensions 0.003"×0.003", to provide a flow such that the pressure inside the vessel does not exceed 50 psi.) Fluid is pumped through the guidewire 420 and out of the holes 460 (which may advantageously be 50–300 microns in diameter) to flush away emboli from the treated lesion 410N and down the external carotid 402, or to localize drugs to a desired treatment location. The guidewire 420 may have a single lumen (not shown) that is in fluid communication with both the internal carotid artery 400 (via the holes 460) and the occlusive device 422, in which case the irrigation fluid and the fluid used to inflate the occlusive device 422 are the same. Alternatively, the guidewire 420 may have dedicated lumens (not shown) for irrigation and inflation.

Instead of pumping irrigation fluid through the holes 460 as shown in FIG. 13, a larger slot (not shown) of dimensions 0.005"×0.100–0.200" may be cut into the guidewire 420 and then covered with a braid (not shown) that extends 0.010–0.030" beyond the edges of the slot. As irrigation fluid is passed through the guidewire 420, the braid expands, permitting the irrigation fluid to pass out of the slot and into the internal carotid 400. Instead of using a braid, this slot may alternatively be covered with a plastic sheath (not shown) having a plurality of slits or pores (not shown) which are in fluid communication with the slot. Ten pores having a diameter of 50–100 microns may advantageously be used.

Fluid flow rates for the methods disclosed in FIGS. 12 and 13 are preferably between about 0.1 cc/sec and 10 cc/sec, more preferably about 0.1 cc/sec and 3 cc/sec, more preferably between about 0.5 and 1.5 cc/sec, and still more preferably about 1 cc/sec. The fluid pressure may be pulsed on and off to better flush away emboli or treat the occlusion. For example, fluid pressure may be alternately applied for 5 seconds (in the form a pulse) and then turned off for 2–3 seconds.

Further details regarding the devices of FIGS. 12 and 13 and other devices and methods are described in Applicant's copending application entitled METHOD FOR CONTAINING AND REMOVING OCCLUSIONS IN THE CAROTID ARTERIES, Ser. No. 09/270,150, filed Mar. 16, 1999, the entirety of which is hereby incorporated by reference.

The preferred methods of the invention can be used especially following myocardial infarction, for totally occluded vessels and partially occluded vessels defined by TIMI 0–1 flow, and having no major side branch. However, the method is not intended to be limited only to such applications, and may also be used for vessels having blood flow through side branches. TIMI stands for "thrombolysis in myocardial infarction." This value is measured angiographically by injecting a dye and noting the time it takes to clear through the blood vessel. A TIMI of 3 means that the vessel is open. A TIMI of 0 means that the vessel is totally occluded. In a totally occluded vessel, one cannot visualize past the site of the occlusion because the dye will not flow past the occlusion. Because the site cannot be visualized, a distal occlusive device generally cannot be used unless the occlusion is dissolved using methods such as described above.

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

What is claimed is:

1. A method for treating an intravascular occlusion, comprising:
   delivering a catheter having a proximal end and a distal end and a lumen extending therethrough into a blood vessel to a site near the intravascular occlusion, the catheter having an occlusive device on the distal end;
   actuating the occlusive device at a location distal to the intravascular occlusion to at least partially occlude blood flow through the vessel; and
   delivering a drug-containing fluid through the lumen of the catheter and out through at least one hole in a proximal face of the occlusive device such that the fluid is delivered in a distal to proximal direction.

2. The method of claim 1, wherein the drug-containing fluid is delivered through a plurality of holes in the proximal face of the occlusive device.

3. The method of claim 1, wherein the occlusive device is a balloon.

4. The method of claim 1, wherein the drug-containing fluid is delivered at a flow rate of between about 0.1 to 3 cc/second.

5. A method for treating an intravascular occlusion, comprising:
   delivering a catheter having a proximal end and a distal end and a lumen extending therethrough into a blood vessel to a site near the intravascular occlusion, the catheter having a balloon on the distal end;
   inflating the balloon at a location distal to the intravascular occlusion to at least partially occlude blood flow through the vessel; and
   delivering a drug-containing fluid through a plurality of holes in a proximal face of the balloon and across the intravascular occlusion in a distal to proximal direction, the drug being injected through the lumen of the catheter.

6. The method of claim 5, wherein the drug-containing fluid delivered through the lumen is used to inflate the balloon.

* * * * *